US008722584B2

(12) United States Patent
Delisa et al.

(10) Patent No.: US 8,722,584 B2
(45) Date of Patent: May 13, 2014

(54) GENETIC SELECTION FOR PROTEIN FOLDING AND SOLUBILITY IN THE BACTERIAL PERIPLASM

(75) Inventors: Matthew P. Delisa, Ithaca, NY (US); Thomas J. Mansell, Ithaca, NY (US); Adam C. Fisher, Ithaca, NY (US)

(73) Assignee: Cornell University, Ithaca, NY (US)

( * ) Notice: Subject to any disclaimer, the term of this patent is extended or adjusted under 35 U.S.C. 154(b) by 13 days.

(21) Appl. No.: 12/522,634

(22) PCT Filed: Jan. 14, 2008

(86) PCT No.: PCT/US2008/050991
§ 371 (c)(1),
(2), (4) Date: Feb. 17, 2010

(87) PCT Pub. No.: WO2008/089132
PCT Pub. Date: Jul. 24, 2008

(65) Prior Publication Data
US 2010/0144546 A1  Jun. 10, 2010

Related U.S. Application Data

(60) Provisional application No. 60/880,312, filed on Jan. 12, 2007.

(51) Int. Cl.
*C40B 30/00* (2006.01)

(52) U.S. Cl.
USPC ............... 506/14; 506/10; 435/29; 435/320.1

(58) Field of Classification Search
None
See application file for complete search history.

(56) References Cited

U.S. PATENT DOCUMENTS

| | | | |
|---|---|---|---|
| 5,935,824 A | 8/1999 | Sgarlato | |
| 5,990,275 A | 11/1999 | Whitlow et al. | |
| 6,867,042 B2 | 3/2005 | Waldo | |
| 6,936,421 B2 | 8/2005 | Anderson | |
| 7,252,952 B2 | 8/2007 | Lorens | |
| 2002/0110860 A1 | 8/2002 | Bron et al. | |
| 2003/0064435 A1 | 4/2003 | Weiner | |
| 2003/0096306 A1 | 5/2003 | Maur et al. | |
| 2003/0180937 A1 | 9/2003 | Georgiou et al. | |
| 2003/0219870 A1 | 11/2003 | Georgiou | |
| 2004/0077090 A1 | 4/2004 | Short | |
| 2005/0124010 A1 | 6/2005 | Short et al. | |
| 2005/0182138 A1 | 8/2005 | John et al. | |
| 2006/0078875 A1 | 4/2006 | Benkovic | |
| 2007/0026012 A1 | 2/2007 | DeLisa | |
| 2008/0287315 A1 | 11/2008 | Delisa | |
| 2009/0220952 A1 | 9/2009 | Delisa | |
| 2009/0298089 A1 | 12/2009 | Rossner | |

FOREIGN PATENT DOCUMENTS

| | | |
|---|---|---|
| WO | 9222657 | 12/1992 |
| WO | 03083056 | 10/2003 |
| WO | 2004050871 | 6/2004 |

OTHER PUBLICATIONS

Genetic selection for protein solubility enabled by the folding quality control feature of the twin-arginine translocation pathway Protein Science (2006), 15:449-458, Feb. 1, 2006 (on line publication).*
Gerth et al. (A second-generation system for unbiased reading frame selection Protein Engineering, Design and Selection (2004) 17 (7): 595-602.*
Lutz et al Universal vector-based system for nucleic acid reading frame selection Protein Engineering vol. 15, 2002, pp. 1025-1030).*
Wurth et al (Mutations that reduce aggregation of Alzheimer's Aβ-42 peptide: An unbiased search for the sequence determinants of Amyloidogenesis (J. Mol. Biol. 319: 1279-1290.*
Choi et al (App. Microbiol Biotechnol (2004) 64: 625-635) and Shih et al (High-throughput screening of soluble recombinant proteins (Protein Science (2002) 11:1714-1719.*
Clark F. SchierleThe DsbA Signal Sequence Directs Efficient, Cotranslational Export of Passenger Proteins to the *Escherichia coli* Periplasm via the Signal Recognition Particle Pathway Journal of Bacteriology, Oct. 2003, p. 5706-5713.*
Arie et al., 2001, "Chaperone function of FkpA, a heat shock prolyl isomerase, in the periplasm of *Escherichia coli*", Mol Microbiol, 39: 199-210.
Bothmann and Pluckthun, 1998, "Selection for a periplasmic factor improving phage display and functional periplasmic expression", Nat Biotechnol, 16: 376-380.
Bowden et al., 1991, "Structure and morphology of protein inclusion bodies in *Escherichia coli*", Biotechnology (N Y), 9: 725-730.
Broome-Smith, 1990, "Beta-lactamase as a probe of membrane portien assembly and protein export", Molecular Microbiology, 4: 1637-1644.
DeLisa et al., 2002, Genetic analysis of the twin arginine translocator secretion pathway in bacteria, J Biol Chem, 277: 29825-29831.
Dyson et al., 2004, "Production of soluble mammalian proteins in *Escherichia coli*: identification of protein features that correslate with successful expression", BMC Biotechnol 4, 32.
Feilmeier et al., 2000, "Green fluorescent protein functions as a reporter for protein localization in *Escherichia coli*", J Bacteriol, 182: 4068-4076.

(Continued)

*Primary Examiner* — Kagnew H Gebreyesus
(74) *Attorney, Agent, or Firm* — Casimir Jones, S.C.

(57) ABSTRACT

The present invention relates to the fields of microbiology, molecular biology and protein biochemistry. More particularly, it relates to compositions and methods for analyzing and altering (e.g., enhancing or inhibiting) protein folding and solubility (e.g., within periplasm). The present invention provides an engineered assay for protein folding and solubility in the *E. coli* periplasm based on co-translational translocation of a chimera comprising a protein of interest fused to TEM-I β-lactamase that is targeted for export via the signal recognition particle (SRP)-dependent pathway. Using an array of native and heterologous proteins, it is demonstrated that periplasmic folding behavior of proteins is intimately coupled to in vivo β-lactamase activity. As a result of this coupling, the reporter is useful for (1) facile discovery of extrinsic periplasmic factors that affect protein folding and solubility; and (2) genetic selection of solubility-enhanced proteins.

12 Claims, 4 Drawing Sheets

(56) References Cited

OTHER PUBLICATIONS

Fisher et al, 2006, "Genetic selection for protein solubility enabled by the folding quality control feature of the twin-arginine translocation pathway", Protein Science, 15: 449-458.

Frech et al., 1996, "Competition between DsbA-mediated oxidation and conformational folding of RTEM1 beta-lactamase", Biochemistry, 35: 11386-11395.

Missiakas et al., 1996, "New components of protein folding in extracytoplasmic compartments of Escherichia coli SurA, FkpA and Skp/OmpH", Mol Micorbiol, 21: 871-884.

Schierle, 2003, "The DsbA Signal Sequence Directs Efficient, Cotranslational Export of Passenger Proteins to the Escherichia coli Periplasm via the Signal Recognition Particle Pathway", J Bacteriol., 185: 5706-5713.

Sone et al., 1997, Roles of disulfide bonds in bacterial alkaline phosphatase, J Biol Chem, 272: 6174-6178.

Steiner et al., 2006, "Signal sequences directing cotranslational translocation expand the range of proteins amenable to phage display", Nat Biotechnol, 24: 823-831.

Tomoyasu et al., 2001, "Genetic dissection of the roles of chaperones and proteases in protein folding degradation in the Escherichia coli cytosol", Mol Microbiol, 40: 397-413.

Villaverde and Carrio, 2003, "Protein aggregation in recombinant bacteria: biological role of inclusion bodies", Biotechnol Lett, 25: 1385-1395.

Brondijk, et al., "NapGH components of the periplasmic nitrate reductase of Escherichia coli K-12: location, topology and physiological roles in quinol oxidation and redox balancing", Biochemical Journal, vol. 379, No. Part 1, Apr. 1, 2004, pp. 47-55.

Department of Biomedical Engineering: "2004-2005 Annual Report" [Online]—2005, pp. 1-60, XP002496810; The University of Texas at Austin, Retrieved from the Internet: URL: http://www.bme.utexas.edu/pdf/BME%20Annual%202004-2005.pdf> [retrieved on Sep. 23, 2008].

Dubini et al, "Assembly of Tat-dependent [NiFe] hydrogenases: identification of precursor-binding accessory proteins", Febs Letters, Elsevier, Amsterdam, NL, vol. 549, No. 1-3, Aug. 14, 2003, pp. 141-146.

European Search Report for Application No. EP06/789929; Dated Sep. 23, 2008.

International Search Report for Application No. PCT/US06/32810; Dated Mar. 6, 2007.

Strauch et al: "Towards functional genomics: A novel two-hybrid system using the TAT machinery", American Chemical Society. Abstracts of Paper. At The National Meeting, American Chemical Society, Washington DC, US, vol. 229, No. Part 1, Mar. 17, 2005, p. U228.

Collard (Belgian Biosafety Server, http://www.antibioresistance.be/betalactamases.html (1999).

Seehaus et al, Gene, 114: 235-237 (1992).

Georgiou and Valax, "Expression of correctly folded proteins in Escherichia coli" Curr Opinion Biotechnolol 7, 190-197 (1996).

Maxwell et al, "A simple in vivo assay for increased protein solubility," Protein Sci 8, 1908-1911 (1999).

Waldo et al, "Rapid protein-folding assay using green fluorescent protein," Nat Biotechnolol 17, 691-695 (1999).

Cabantous et al, "Protein tagging and detection with engineered self-assembling fragments of green fluorescent protein," Nat Biotechnol 23, 102-107 (2005).

Wigley et al, "Protein solubility and folding lllonitored in vivo by structural cOlllplelllentation of a genetic lllarker protein," Nat Biotechnol 19, 131-136 (2001).

Lesley et al, Protein Eng 15, 153-160 (2002).

Tsumoto et al, "Solubilization of active green fluorescent protein from insoluble particles by guanidine and arginine," Biochem Biophys Res Commun 312, 1383-1386 (2003).

Roodveldt et al, Curr Opinion Struct Biol 15, 50-56 (2005).

Wall et al "Effects of overexpressing folding modulators on the in vivo folding of. heterologous proteins in Escherichia coli," Curr Opin Biotechnol 6, 507-516 (1995).

Berks, "A common export pathway for proteins binding complex redox cofactors?," Mol Microbiol 22, 393-404 (1996).

Settles et al, "Sec-Independent Protein Translocation by the Maize Hcf106 Protein," Science 278, 1467-1470 (1997).

Weiner et al, "A Novel and Ubiquitous System for Membrane Targeting and Secretion of Cofactor-Containing Proteins," Cell 93, 93-101 (1998).

Sanders et al, "Transport of cytochrome c derivatives by the bacterial Tat protein translocation system" Mol Microbiol 41, 241-246 (2001).

Lutz et al, "A universal, vector-based system for nucleic acid reading-frame Selection," Protein Eng 15, 1025-1030 (2002).

Delisa et al "Folding quality control in the export of proteins by the bacterial twin-arginine translocation pathway," Proc Natl Acad Sci USA 100, 6115-6120 (2003).

Delisa et al, "Genetic Analysis of the Twin Arginine Translocator Secretion Pathway in Bacteria," J Biol Chem 277, 29825-29831 (2002).

Niviere et al, J Gen Microbiol, 138: 2173-2183 (1992).

Smith et al, J Bacteriol, 169: 3321-3328 (1987).

Delisa et al, "Genetic screen for directed evolution of soluble proteins in bacteria" Abstracts of Papers American Chemical Society, vol. 229 (Mar. 2005) p. U243.

Delisa et al, "Molecular engineering of soluble proteins directly living cells" Abstracts of Papers American Chemical Society, vol. 227, Mar. 2004, pp. U208-U209.

Fisher et al, "Reprogramming the bacterial Tat system for monitoring protein folding directly in cells" AICHE Annual Meeting, Conference, Proceedings, pp. 8751 (2004).

Fisher et al, "Genetic selection for protein solubility enabled by the folding quality control feature of the twin-arginine translocation pathway" Protein Science, vol. 15, Mar. 2006 pp. 449-458.

International Search Report for Application No. PCT/US06/29998; Dated Aug. 1, 2008.

European Search Report for Application No. EP06/789138; Dated Apr. 21, 2009.

Examiner's Report for Application No. 2006275415; Dated Oct. 29, 2009.

International Search Report for Application No. PCT/US08/50991; Dated Aug. 12, 2008.

Tullman-Ercek, Danielle et al., "Export pathway selectivity of Escherichia coli twin arginine translocation signal peptides," Journal of Biological Chemistry, vol. 282, No. 11, Mar. 2007, pp. 8309-8316.

Philibert Pascal et al, "Directed evolution of single-chain Fv for cytoplasmic expression using the [beta]-galactosidase complementation assay results in proteins highly susceptible to protease degradation and aggregation," Microbial Cell Factories, Biomed Central, London, NL, vol. 3, No. 1, Dec. 17, 2004, p. 16.

Cattaneo, Antonio, et al., "The Selection of Intracellular Antibodies," TIBTECH (1999) vol. 17, pp. 115-120.

* cited by examiner

GENETIC SELECTION FOR PROTEIN FOLDING AND SOLUBILITY IN THE BACTERIAL PERIPLASM

This invention was made with government support under contract number CBET 0449080 awarded by the National Science Foundation. The government has certain rights in the invention.

FIELD OF THE INVENTION

The present invention relates to the fields of microbiology, molecular biology and protein biochemistry. More particularly, it relates to compositions and methods for analyzing and altering (e.g., enhancing or inhibiting) protein folding and solubility (e.g., within the periplasm).

BACKGROUND OF THE INVENTION

Ever since the inception of recombinant DNA technology, laboratory and preparative expression of heterologous proteins in *Escherichia coli* has been a cornerstone of the biotechnology enterprise. Baneyx, F. & Mujacic, M. Recombinant protein folding and misfolding in *Escherichia coli*. *Nat Biotechnol* 22, 1399-1408 (2004); Swartz, J. R. Advances in *Escherichia coli* production of therapeutic proteins. *Curr. Opin. Biotechnol* 12, 195-201 (2001); Georgiou, G. & Segatori, L. Preparative expression of secreted proteins in bacteria: status report and future prospects. *Curr Opin Biotechnol* 16, 538-545 (2005). Unfortunately, many eukaryotic proteins expressed in the cytoplasm of *E. coli* are prone to misfolding and are subsequently degraded by cellular proteases or deposited into biologically inactive aggregates known as inclusion bodies. Dyson, M. R., Shadbolt, S. P., Vincent, K. J., Perera, R. L. & McCafferty, J. Production of soluble mammalian proteins in *Escherichia coli*: identification of protein features that correlate with successful expression. BMC Biotechnol 4, 32 (2004); Luan, C. H. et al. High-throughput expression of *C. elegans* proteins. Genome Res 14, 2102-2110 (2004); Braun, P. et al. Proteome-scale purification of human proteins from bacteria. Proc Natl Acad Sci USA 99, 2654-2659 (2002); Baker, T. A. & Sauer, R. T. ATP-dependent proteases of bacteria: recognition logic and operating principles. Trends Biochem Sci 31, 647-653 (2006); Tomoyasu, T., Mogk, A., Langen, H., Goloubinoff, P. & Bukau, B. Genetic dissection of the roles of chaperones and proteases in protein folding and degradation in the *Escherichia coli* cytosol. Mol Microbiol 40, 397-413 (2001); Bowden, G. A., Paredes, A. M. & Georgiou, G. Structure and morphology of protein inclusion bodies in *Escherichia coli*. Biotechnology (N Y) 9, 725-730 (1991); Villayerde, A. & Carrio, M. M. Protein aggregation in recombinant bacteria: biological role of inclusion bodies. Biotechnol Lett 25, 1385-1395 (2003).

Misfolding of eukaryotic proteins in the cytoplasm is often a consequence of the relative crowdedness of this compartment where macromolecule concentration can reach 300-400 mg/ml and the requirement for post-translational processing that is absent from the cytoplasm such as disulfide bond formation or glycosylation. Ellis, R. J. & Minton, A. P. Cell biology: join the crowd. Nature 425, 27-28 (2003); Kadokura, H., Katzen, F. & Beckwith, J. Protein disulfide bond formation in prokaryotes. Annu Rev Biochem 72, 111-135 (2003); Weerapana, E. & Imperiali, B. Asparagine-linked protein glycosylation: from eukaryotic to prokaryotic systems. Glycobiology 16, 91R-101R (2006).

To remedy some of these issues, secretion into the periplasm of *E. coli* is often employed because this compartment: (1) contains significantly fewer proteins, especially proteases, compared to the cytoplasm; consequently periplasmic proteins are easier to isolate and are often less prone to crowding-induced aggregation and/or proteolytic degradation; and (2) houses a network of redox enzymes that catalyze the formation and isomerization of disulfide bonds that are essential for the folding and function of many eukaryotic proteins. These advantages notwithstanding, there still remain significant challenges with respect to secretion across the inner membrane, degradation by resident periplasmic proteases and misfolding due to either incorrect disulfide-bond formation or aggregation into periplasmic inclusion bodies. Thus, to address these challenges, new experimental tools are needed for understanding and characterizing the complexities of the periplasmic folding environment and elucidating the factors that impede the folding of proteins in this biological compartment.

SUMMARY OF THE INVENTION

The present invention relates to the fields of microbiology, molecular biology and protein biochemistry. More particularly, it relates to compositions and methods for analyzing and altering (e.g., enhancing or inhibiting) protein folding and solubility (e.g., within the periplasm). Accordingly, in some embodiments, the present invention provides methods of characterizing the folding of a target protein within the periplasm of cells comprising: expressing in a plurality of cells a fusion protein encoded by a nucleic acid sequence comprising a signal sequence, a target protein sequence, and a reporter gene sequence in operable order; and correlating reporter activity to protein folding in the periplasm of the cells. In some embodiments, the correlating step further comprises growing said cells on selective media, wherein said reporter gene sequence allows growth of cells in which said fusion protein is correctly folded and/or soluble in the periplasm of said cells on said selective media. In some embodiments, the amount of growth observed on the selective medium correlates to the solubility and/or ability of the target protein sequence to fold in the periplasm. In some embodiments, the amount of growth is observed for a predetermined amount of time. In other embodiments, the amount of growth is compared to that of a control protein for the solubility and/or ability to fold in the periplasm is known. The present invention is not limited to the use of any particular reporter gene. In some embodiments, the reporter gene encodes antibiotic resistance. In some embodiments, the reporter gene sequence is the beta-lactamase gene sequence. The present invention is not limited to the use of any particular signal sequence. In some embodiments, the signal sequence is an SRP-dependent translocation pathway signal sequence, i.e., a signal sequence that is recognized by the SRP-dependent translocation pathway and causes polypeptides to which it is fused to be exported into the periplasm of a host cell. Examples of SRP-dependent translocation pathway signal sequences include, but are not limited to, DsbAss, TotTss, SfmCss, TolBss, Yralss, CcmHss, FocCss, NikAss, and FlgIss. The present invention is not limited to the use of any particular target protein sequence. In some embodiments, the target protein sequences are wild-type, while in other embodiments, the target protein sequences are variant or mutagenized target protein sequences. In some embodiments, the methods of the present invention further comprise the step of selecting clones of said cells that grow on said selective media. In some embodiments, the target protein sequence is a target protein sequence as identified herein. In other embodiments, the target protein is selected from the group consisting of an amyloid-β peptide and a single-chain Fv antibody fragment.

In some embodiments, the present invention provides methods of screening for protein variants that fold correctly in the periplasm comprising: providing a library of nucleic acid sequences comprising a signal sequence, variant target protein sequence, and reporter sequence in operable combination; expressing said library of nucleic acid sequences in cells; and correlating reporter activity to the correct folding of variant target proteins in the periplasm of the cells. The number of variants that may be screened in the present invention is not limited. In some embodiments, $10^2$, $10^3$, $10^4$, $10^5$, $10^6$, $10^7$, $10^8$, $10^9$ or more variants are screened. In some embodiments, the correlating step further comprises growing said cells on selective media, wherein said reporter gene sequence allows growth of cells in which said fusion protein is correctly folded in the periplasm of said cells on said selective media. In some embodiments, the methods further comprise the step of selecting clones of said cells that grow on said selective media. In some embodiments, the correlating step further comprises growing said cells on selective media, wherein said reporter gene sequence allows growth of cells in which said fusion protein is correctly folded and/or soluble in the periplasm of said cells on said selective media. In some embodiments, the amount of growth observed on the selective medium correlates to the solubility and/or ability of the target protein sequence to fold in the periplasm. In some embodiments, the amount of growth is observed for a predetermined amount of time. In other embodiments, the amount of growth is compared to that of a control protein for the solubility and/or ability to fold in the periplasm is known. The present invention is not limited to the use of any particular reporter gene. In some embodiments, the reporter gene encodes antibiotic resistance. In some embodiments, the reporter gene sequence is the beta-lactamase gene sequence. The present invention is not limited to the use of any particular signal sequence. In some embodiments, the signal sequence is an SRP-dependent translocation pathway signal sequence, i.e., a signal sequence that is recognized by the SRP-dependent translocation pathway and causes polypeptides to which it is fused to be exported into the periplasm of a host cell. Examples of SRP-dependent translocation pathway signal sequences include, but are not limited to, DsbAss, TotTss, SfmCss, TolBss, Yralss, CcmHss, FocCss, NikAss, and FlgIss. The present invention is not limited to the use of any particular target protein sequence. In some embodiments, the target protein sequences are wild-type, while in other embodiments, the target protein sequences are variant or mutagenized target protein sequences. In some embodiments, the target protein sequence is a target protein sequence as identified herein. In other embodiments, the target protein is selected from the group consisting of an amyloid-β peptide and a single-chain Fv antibody fragment.

In further embodiments, the present invention provides methods for high-throughput screening of target proteins that fold correctly in the periplasm comprising: providing a library of nucleic acid sequences comprising a signal sequence, target protein sequence, and reporter sequence in operable combination; introducing said library of nucleic acid sequences into cells; growing said cells on a selective media, wherein said reporter gene sequence allows growth on said selective media of cells in which said fusion protein is correctly folded in the periplasm of said cells; and selecting clones of said cells in which said fusion protein is correctly folded in the periplasm. In some embodiments, the screening described above is combined with other screening methods, such as iterative mutagenesis and selection for other desired properties of the target protein through directed evolution procedures or screening assays for other folding properties, such as processing by the TAT pathway. In some embodiments, first, second, third, fourth or more screening procedures are utilized. In some embodiments, the target protein sequences or sequences in the case of library are shuttled between vectors suitable for use in each successive screening step. In some embodiments, the methods of the present invention further comprise the steps of further culturing said clones of said cells in which said fusion protein is correctly folded in the periplasm and isolating said fusion protein from said cells. In some embodiments, the methods further comprise the steps of subcloning said target protein sequence, expressing the target protein sequence in a desired cell line, and purifying said target protein sequence from said desired cell line.

In further embodiments, the present invention provides a library of cells comprising a plurality of nucleic acid sequences comprising a signal sequence, variant target protein sequence, and reporter sequence in operable combination. The present invention is not limited to the use of any particular reporter gene. In some embodiments, the reporter gene encodes antibiotic resistance. In some embodiments, the reporter gene sequence is the beta-lactamase gene sequence. The present invention is not limited to the use of any particular signal sequence. In some embodiments, the signal sequence is an SRP-dependent translocation pathway signal sequence, i.e., a signal sequence that is recognized by the SRP-dependent translocation pathway and causes polypeptides to which it is fused to be exported into the periplasm of a host cell. Examples of SRP-dependent translocation pathway signal sequences include, but are not limited to, DsbAss, TotTss, SfmCss, TolBss, Yralss, CcmHss, FocCss, NikAss, and FlgIss. The present invention is not limited to the use of any particular target protein sequence. In some embodiments, the target protein sequences are wild-type, while in other embodiments, the target protein sequences are variant or mutagenized target protein sequences. In some embodiments, the target protein sequence is a target protein sequence as identified herein. In other embodiments, the target protein is selected from the group consisting of an amyloid-β peptide and a single-chain Fv antibody fragment.

In some embodiments, the present invention provides a library of cells comprising a plurality of nucleic acid sequences comprising a signal sequence, target protein sequence, and reporter sequence in operable combination, wherein said plurality of nucleic acid sequences comprise different target protein sequences. The present invention is not limited to the use of any particular reporter gene. In some embodiments, the reporter gene encodes antibiotic resistance. In some embodiments, the reporter gene sequence is the beta-lactamase gene sequence. The present invention is not limited to the use of any particular signal sequence. In some embodiments, the signal sequence is an SRP-dependent translocation pathway signal sequence, i.e., a signal sequence that is recognized by the SRP-dependent translocation pathway and causes polypeptides to which it is fused to be exported into the periplasm of a host cell. Examples of SRP-dependent translocation pathway signal sequences include, but are not limited to, DsbAss, TotTss, SfmCss, TolBss, Yralss, CcmHss, FocCss, NikAss, and FlgIss. The present invention is not limited to the use of any particular target protein sequence. In some embodiments, the target protein sequences are wild-type, while in other embodiments, the target protein sequences are variant or mutagenized target protein sequences. In some embodiments, the target protein sequence is a target protein sequence as identified herein. In other embodiments, the target protein is selected from the group consisting of an amyloid-β peptide and a single-chain Fv antibody fragment.

In some embodiments, the present invention provides a library of nucleic acid sequences comprising a signal sequence, variant target protein sequence, and reporter sequence in operable combination. The present invention is not limited to the use of any particular reporter gene. In some embodiments, the reporter gene encodes antibiotic resistance. In some embodiments, the reporter gene sequence is the beta-lactamase gene sequence. The present invention is not limited to the use of any particular signal sequence. In some embodiments, the signal sequence is an SRP-dependent translocation pathway signal sequence, i.e., a signal sequence that is recognized by the SRP-dependent translocation pathway and causes polypeptides to which it is fused to be exported into the periplasm of a host cell. Examples of SRP-dependent translocation pathway signal sequences include, but are not limited to, DsbAss, TotTss, SfmCss, TolBss, Yralss, CcmHss, FocCss, NikAss, and FlgIss. The present invention is not limited to the use of any particular target protein sequence. In some embodiments, the target protein sequences are wild-type, while in other embodiments, the target protein sequences are variant or mutagenized target protein sequences. In some embodiments, the target protein sequence is a target protein sequence as identified herein. In other embodiments, the target protein is selected from the group consisting of an amyloid-β peptide and a single-chain Fv antibody fragment.

In some embodiments, the present invention provides a library of nucleic acid sequences comprising a signal sequence, target protein sequence, and reporter sequence in operable combination, wherein said plurality of nucleic acid sequences comprise different target protein sequences. The present invention is not limited to the use of any particular reporter gene. In some embodiments, the reporter gene encodes antibiotic resistance. In some embodiments, the reporter gene sequence is the beta-lactamase gene sequence. The present invention is not limited to the use of any particular signal sequence. In some embodiments, the signal sequence is an SRP-dependent translocation pathway signal sequence, i.e., a signal sequence that is recognized by the SRP-dependent translocation pathway and causes polypeptides to which it is fused to be exported into the periplasm of a host cell. Examples of SRP-dependent translocation pathway signal sequences include, but are not limited to, DsbAss, TotTss, SfmCss, TolBss, Yralss, CcmHss, FocCss, NikAss, and FlgIss. The present invention is not limited to the use of any particular target protein sequence. In some embodiments, the target protein sequences are wild-type, while in other embodiments, the target protein sequences are variant or mutagenized target protein sequences. In some embodiments, the target protein sequence is a target protein sequence as identified herein. In other embodiments, the target protein is selected from the group consisting of an amyloid-β peptide and a single-chain Fv antibody fragment.

In some embodiments, the present invention provides a nucleic acid sequence encoding a signal sequence, target protein sequence, and reporter sequence in operable combination. In some embodiments, the nucleic acid sequence comprises a multiple cloning site and the target protein sequence is inserted into the multiple cloning site. In other embodiments, the present invention provides a nucleic acid sequence comprising in 5' to 3' order or other operable association a SRP-dependent translocation signal sequence, multiple cloning site, and a reporter gene sequence, wherein a target protein of interest may be introduced into the multiple cloning site. The present invention is not limited to the use of any particular reporter gene. In some embodiments, the reporter gene encodes antibiotic resistance. In some embodiments, the reporter gene sequence is the beta-lactamase gene sequence. The present invention is not limited to the use of any particular signal sequence. In some embodiments, the signal sequence is an SRP-dependent translocation pathway signal sequence, i.e., a signal sequence that is recognized by the SRP-dependent translocation pathway and causes polypeptides to which it is fused to be exported into the periplasm of a host cell. Examples of SRP-dependent translocation pathway signal sequences include, but are not limited to, DsbAss, TotTss, SfmCss, TolBss, Yralss, CcmHss, FocCss, NikAss, and FlgIss. The present invention is not limited to the use of any particular target protein sequence. In some embodiments, the target protein sequences are wild-type, while in other embodiments, the target protein sequences are variant or mutagenized target protein sequences. In some embodiments, the target protein sequence is a target protein sequence as identified herein. In other embodiments, the target protein is selected from the group consisting of an amyloid-β peptide and a single-chain Fv antibody fragment.

In some embodiments, the present invention provides vectors comprising the foregoing nucleic acid sequences. In some embodiments, the vectors are linear, while in other embodiments, the vectors are circular.

In some preferred embodiments, the vectors are plasmids. In some embodiments, the present invention further provides kits comprising one or more of the foregoing nucleic acid sequences and/or vectors. In some embodiments, the nucleic acid sequences or vectors are in a container in the kit. In some embodiments, the kits comprise a control vector or nucleic acid sequence that has a fusion protein containing a target protein with known solubility in the periplasm or a known ability to fold in the periplasm. In some embodiments, one or more control sequences are provided, wherein the control sequence comprise a control sequence with low solubility/folding ability, intermediate solubility/folding ability, or high solubility/folding ability in the periplasm of a host cell. In some embodiments, the kits further comprise a container of host cells. In some embodiments, the host cells are competent. In further embodiments, the kits comprise instructions for performing the assays and screen methods described above.

DEFINITIONS

Figure 1:
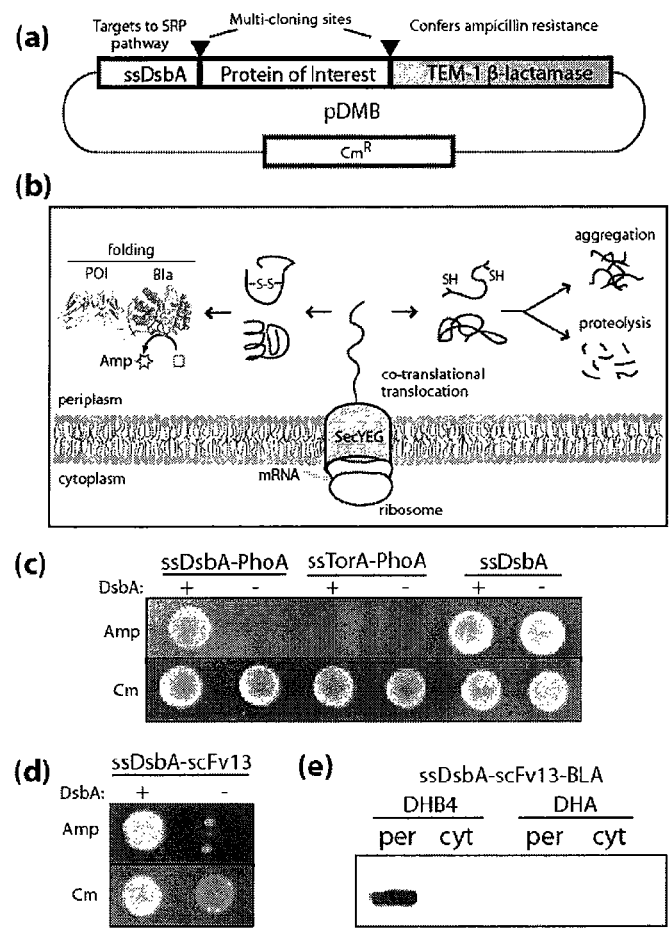
FIG. 1. Reporter construction and assay of redox-dependent folding. (a) The plasmid pDMB includes a tripartite fusion of N-terminal signal sequence from *E. coli* DsbA, the protein of interest, and TEM-1 Bla. (b) The DsbA signal sequence allows for co-translational translocation across the cytoplasmic membrane via the SRP-dependent pathway. Once the nascent polypeptide enters the periplasm it can fold properly, conferring ampicillin-resistance, or it can misfold, in which case it becomes subject to cellular quality control mechanisms such as aggregation and proteolysis. (c) DHB4 cells (DsbA+) and DHA cells (DsbA−) were transfected with plasmids expressing either ssDsbA-PhoA-Bla, ssTorA-PhoA-Bla, ssDsbA-Bla and spot plated on LB/agar containing either 50 μg/ml chloramphenicol or 100 μg/ml ampicillin at a dilution of 10-fold from overnight cultures. (d) Same as in (c), except cells expressed ssDsbA-scFv13-Bla. (e) Western blotting of subcellular fractions DHB4 and DHA cells expressing ssDsbA-scFv13-Bla. Samples were blotted with anti-Bla serum. Cyt, cytoplasmic fraction; Per, periplasmic fraction.

To facilitate an understanding of the invention, a number of terms are defined below.

As used herein, the term "target protein" when used in reference to a protein or nucleic acid refers to a protein or nucleic acid encoding a protein of interest for which solubility and/or folding is to be analyzed and/or altered of the present invention. The term "target protein" encompasses both wild-type proteins and those that are derived from wild type proteins (e.g., variants of wild-type proteins or polypeptides, or, chimeric genes constructed with portions of target protein coding regions), and further encompass fragments of a wild-type protein. Thus, in some embodiments, a "target protein" is a variant or mutant. The present invention is not limited by the type of target protein analyzed.

As used herein, the term "fusion protein" refers to a polypeptide sequence, and nucleic acid molecules encoding the same, comprising a signal peptide recognized by the Signal Particle Recognition (SRP) pathway, a target protein and a reporter protein. Multiple signal peptides are known in the art and are contemplated to be useful in the present invention. The present invention contemplates that the fusion protein may be under the control of an inducible, a constitutively active, or other promoter.

The invention is not limited by the type of marker protein. As used herein, the terms "reporter protein sequence" or "selectable marker sequence" or "reporter sequence" refer to a nucleic acid sequence (e.g., gene) that encodes an activity (e.g., an enzymatic activity) that confers the ability to grow in medium lacking what would otherwise be an essential nutrient (e.g. the HIS3 gene in yeast cells); in addition, a "reporter protein sequence" or "selectable marker sequence" may confer resistance to an antibiotic or drug upon the cell in which the selectable marker is expressed. The present invention contemplates the use of a reporter protein or selective marker in plasmids comprising nucleic acid sequences encoding a fusion protein, as well as use of a marker protein or selective marker within the nucleic acid sequence encoding the fusion protein itself.

For example, host cells comprising a nucleic acid encoding a fusion protein may grow in a selective environment (e.g., when exposed to an antibiotic) because the nucleic acid encoding a fusion protein (e.g., comprising a marker protein) encodes activity (e.g., β-lactamase activity) that confers resistance to the antibiotic.

As used herein, the term "instructions for using said kit for said monitoring the folding and/or solubility of a target protein" includes instructions for using the reagents contained in the kit for monitoring the solubility and/or folding (e.g., through the growth of host cells in the presence of a selectable marker) of a target protein.

As used herein, the term "solubility profile" refers to the solubility and/or folding properties of a target protein, wherein the solubility and/or folding properties of a target protein are monitored by measuring the ability of host cells, comprising a fusion protein that comprises a target protein, to grow in the presence of a drug, antibiotic, or other selective pressure (e.g., in the presence of ampicillin). In preferred embodiments, the ability of host cells to grow in the presence of the drug, antibiotic, or other selective pressure is indicative of the solubility of the target protein, whereas, the absence of host cell growth is indicative of the insolubility of the target protein. The solubility profiles of the present invention find use in, among other things, the characterization of target protein solubility and/or folding, mutant target protein solubility and/or folding, and the effect of candidate compositions on the solubility and/or folding of a target protein. In preferred embodiments, a solubility profile detects intermediate ranges of solubility (e.g., via correlating the relative growth rate of host cells comprising a fusion protein of the present invention in the presence of a drug, antibiotic, or other selective pressure with the relative periplasmic expression, i.e., the solubility, of the fusion protein comprising the target protein and a marker protein).

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of a sample (e.g., a nucleic acid encoding a fusion protein of the present invention) to a desired cell or tissue. As used herein, the term "adenovirus gene transfer system" refers to gene transfer systems comprising intact or altered viruses belonging to the family Adenoviridae.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion thereof. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the terms "target protein gene" or "target protein genes" refer to the full-length target protein sequence. However, it is also intended that the term encompass fragments of the target protein sequences, mutants of the target protein sequences, as well as other domains within the full-length target protein nucleotide sequences. Furthermore, the terms "target protein nucleotide sequence" or "target protein polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics (e.g., increased or decreased solubility) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

As used herein, the term "recombinant DNA molecule" as used herein refers to a DNA molecule that is comprised of segments of DNA joined together by means of molecular biological techniques.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. The present invention is not limited to naturally occurring protein molecules. For example, the present invention contemplates synthesis of fusion proteins comprising multiple regions of unique polypeptide sequences (e.g., a Tat leader sequence, a target protein sequence, and marker protein sequence).

The term "isolated" when used in relation to a protein, as in "an isolated protein" or refers to a protein that is identified and separated from at least one component or contaminant with which it is ordinarily associated in its natural source.

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973)), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The term "candidate agent" may be any substance that potentially inhibits or enhances protein folding and/or solubility, including, but not limited to, any chemical entity, pharmaceutical, drug, and the like (e.g., a small molecule or compound). Candidate agents may include fragments or parts of naturally-occurring proteins or compounds, or may be found as active combinations of known proteins or compounds, which are otherwise inactive. It is to be understood that candidate agents comprise both known and potential solubility inhibiting or enhancing agents. A candidate agent can be determined to be capable of altering target protein solubility and/or folding using the methods of the present invention.

As used herein, the term "host cell" refers to any cell, whether located in vitro or in vivo, that can be, or has been, a recipient for or incorporates exogenous nucleic acid sequences (e.g., vectors comprising fusion protein sequence), polynucleotides and/or proteins of the present invention. It is also meant to include progeny of a single cell, and the progeny may not necessarily be completely identical (e.g., in morphology or in genomic or total DNA complement) to the original parent cell due to natural, accidental, or deliberate mutations. The cells may be eukaryotic or prokaryotic and include, but are not limited to bacterial cells (e.g., *E. coli*) yeast cells, mammalian cells, avian cells, amphibian cells, plant cells, fish cells, and insect cells).

DETAILED DESCRIPTION OF THE INVENTION

Over the last decade, several powerful methods have been reported that enable experimental observation of protein folding and solubility at physiological concentrations in the background of all cellular constituents. A common feature shared by these approaches is the coupling of the conformational state of a protein of interest (POI) with a signal that can be detected above the cellular background. Such methods include: transcriptional fusion reporters that signal the cell's genetic response to misfolding and aggregation of the POI; and translational fusions between the POI and a reporter peptide (e.g., tetracysteine motif binding site), protein (e.g., chloramphenicol acteyltransferase, green fluorescent protein (GFP)) or split protein fragment (e.g., β-galactosidase, GFP) whose activity is modulated by the folding behavior and solubility profile of the POI. Kraft, M. et al. An online monitoring system based on a synthetic sigma32-dependent tandem promoter for visualization of insoluble proteins in the cytoplasm of *Escherichia coli*. Appl Microbiol Biotechnol (2007); Ignatova, Z. & Gierasch, L. M. Monitoring protein stability and aggregation in vivo by real-time fluorescent labeling. Proc Natl Acad Sci USA 101, 523-528 (2004); Maxwell, K. L., Mittermaier, A. K., Forman-Kay, J. D. & Davidson, A. R. A simple in vivo assay for increased protein solubility. Protein Sci 8, 1908-1911 (1999); Waldo, G. S., Standish, B. M., Berendzen, J. & Terwilliger, T. C. Rapid protein-folding assay using green fluorescent protein. Nat Biotechnol 17, 691-695 (1999); Wigley, W. C., Stidham, R. D., Smith, N. M., Hunt, J. F. & Thomas, P. J. Protein solubility and folding monitored in vivo by structural complementation of a genetic marker protein. Nat Biotechnol 19, 131-136 (2001); Cabantous, S., Terwilliger, T. C. & Waldo, G. S. Protein tagging and detection with engineered self-assembling fragments of green fluorescent protein. Nat Biotechnol 23, 102-107 (2005). Along similar lines, we recently developed a protein folding and solubility reporter (where "solubility" here is defined as the thermodynamic solubility of a protein and its susceptibility to aggregation and degradation by proteases) that exploits the authentic protein folding quality control mechanism of the *E. coli* twin-arginine translocation (Tat) pathway. Fisher, A. C., Kim, W. & DeLisa, M. P. Genetic selection for protein solubility enabled by the folding quality control feature of the twin-arginine translocation pathway. Protein Sci 15, 449-458 (2006). In this system, POIs were expressed as a sandwich fusion between an N-terminal Tat signal peptide and a C-terminal mature TEM-1 β-lactamase (Bla). Since attainment of a native conformation is a prerequisite for transport via the bacterial Tat pathway, only properly folded POIs were observed to co-localize Bla into the periplasm, thereby conferring an ampicillin-resistant phenotype to *E. coli* cells. DeLisa, M. P., Tullman, D. & Georgiou, G. Folding quality control in the export of proteins by the bacterial twin-arginine translocation pathway. *Proc Natl Acad Sci USA* 100, 6115-6120 (2003). It is particularly noteworthy, however, that all of the above protein folding assays report on the conformational explorations of a POI in the cytoplasm; there are currently no existing assays for monitoring protein folding in the bacterial periplasm.

Accordingly, the present invention provides an engineered assay, based on the bacterial signal recognition particle (SRP)-dependent translocation pathway, that reliably reports the folding behavior of POIs expressed in the periplasm. The SRP pathway is useful because it has the unique property of co-translational translocation whereby nascent polypeptides bearing N-terminal SRP export signals are directly translated across the inner membrane by a ribosome-SecYEG complex. Macfarlane, J. & Muller, M. The functional integration of a polytopic membrane protein of *Escherichia coli* is dependent on the bacterial signal-recognition particle. Eur J Biochem 233, 766-771 (1995); Valent, Q. A. et al. The *Escherichia coli* SRP and SecB targeting pathways converge at the translocon. EMBO J. 17, 2504-2512 (1998); Powers, T. & Walter, P. Co-translational protein targeting catalyzed by the *Escherichia coli* signal recognition particle and its receptor. EMBO J. 16, 4880-4886 (1997). As a result, SRP-targeted proteins experience minimal residence time in the cytoplasm, thus ensuring that folding events take place predominantly in the periplasmic space. In preferred embodiments, the reporter comprises a tripartite fusion between (1) the N-terminal signal peptide from *E. coli* DsbA that has previously been shown to direct proteins through the SRP-dependent pathway, (2) the POI, and (3) a C-terminal fusion of mature TEM-1 Bla. Schierle, C. F. et al. The DsbA signal sequence directs efficient, cotranslational export of passenger proteins to the *Escherichia coli* periplasm via the signal recognition particle pathway. J Bacteriol 185, 5706-5713 (2003).

Using this construction in combination with simple selection on β-lactam antibiotics, a tight coupling was observed between the periplasmic folding behavior of the POI and Bla activity. Consequently, it was possible to reliably discriminate between folded and misfolded conformations where the latter arose due to aggregation, kinetic limitations on folding, lack of disulfide bond formation, and lack of chaperone-assisted folding. In addition, the assay was capable of evaluating cellular factors that influence protein folding and solubility in the periplasm, such as molecular chaperones and N-linked protein glycosylation. Finally, we demonstrate that the assay can be used as part of a directed evolution strategy to efficiently interrogate combinatorial libraries for the presence of protein sequences that exhibit increased solubility in the periplasmic space.

Given the importance of protein folding to myriad biological applications, it is not surprising that several methods of monitoring protein folding and solubility have been engineered. However, while many reporters have been shown to be effective as reporters of folding behavior (e.g., solubility, aggregation, inclusion body formation), all reported folding occurs in the cytoplasm of *E. coli*. At present, there are no reports of cell-based assays for monitoring protein folding in extracytoplasmic compartments such as the periplasmic space.

Accordingly, the present invention provides a genetic selection for periplasmic protein solubility and folding in vivo (e.g., using the signal recognition particle (SRP)-dependent pathway). One advantage conferred by use of the SRP-dependent pathway is that target proteins are extruded directly into the periplasm without residence time in the cytoplasmic folding environment. Using this system, the present invention has the ability to characterize the in vivo periplasmic folding and solubility of several classes of proteins including, but not limited to, amyloid-β peptides and single-chain Fv antibody fragments. In addition, the present invention provides the potential for the directed evolution of proteins in the periplasm. Finally, by coupling this SRP-dependent folding assay with a previously developed cytoplasmic folding assay based on the Tat-dependent pathway, it is possible to observe, in an unbiased manner, the difference in the folding environments of the cytoplasmic and periplasmic cellular compartments. In some embodiments, the application of this system is geared toward unbiased whole-cell screening of combinatorial libraries to determine the optimal folding environment for heterologously expressed proteins.

The present invention further provides a method for reporting in vivo protein folding in the periplasm of bacteria (e.g., Gram-negative bacteria). In some embodiments, the present invention provides a method that involves a tripartite fusion between signal sequence, target protein, and beta-lactamase to correlate beta-lactamase activity to protein folding. Thus, in some embodiments, the present invention provides an assay for monitoring protein folding and solubility in an extracellular location (e.g., the bacterial periplasm). Accordingly, in some embodiments, an assay of the present invention is utilized with one or more proteins that are expressed in the periplasm. Thus, in some embodiments, compositions and methods of the present invention are utilized in commercial applications (e.g., in the production, engineering and manufacture of protein therapeutics).

Proteins expressed through recombinant means often misfold, particularly in prokaryotic host cells that lack the processing machinery of an eukaryotic cell. When a protein misfolds, it often becomes less soluble, and may precipitate in the cell as an inclusion body. Additionally, mutations in naturally occurring proteins increase the rate of misfolding when endogenously expressed, as well as when exogenously expressed in a recombinant host cell. Additionally, several diseases, such as Alzheimer's disease, Parkinson's disease, Huntington's disease, and others are thought to be the result of, or associated with protein misfolding in vivo. In certain embodiments, the present invention provides a method for assaying for the presence of target protein misfolding in a living cell (e.g., a bacterial cell).

The invention also provides methods for determining the solubility of a target polypeptide. In some embodiments, the present invention provides a method for assessing protein solubility and/or folding comprising providing a nucleic acid encoding a fusion protein comprising a SRP-dependent pathway signal sequence, a target protein, and a reporter protein; expressing the fusion protein in host cells (e.g., bacterial cells); and correlating the ability of the host cells to grow in the presence of a selective agent (e.g., ampicillin) with the solubility and/or folding of the target protein. In preferred embodiments, growth of host cells is indicative of a soluble and/or properly folded target protein.

In some embodiments, the fusion protein comprises a SRP-dependent pathway signal sequence, a target protein, and TEM1 β-lactamase (Bla). In some embodiments, the present invention further provides methods for identifying mutations in a cell that alter the solubility of a target protein.

Although the present invention is not limited to any particular mechanism, and the present invention contemplates a variety of mechanisms, it is believed that, in some embodiments, a target protein that is soluble and/or that folds correctly is directly exported from the cytoplasm to the periplasm via the SRP-dependent pathway, folds in the periplasm, and, by virtue of the reporter protein (e.g., Bla protein) fusion, confers resistance (e.g., ampicillin resistance) to host cells (e.g., *E. coli*) expressing the fused protein. In preferred embodiments, discrimination between folded and misfolded target sequences is accomplished due to the fact that only correctly folded proteins have reporter protein activity (e.g., selectable activity). When the correctly folded fusion protein is present in the periplasm, the cells expressing those fusion proteins either grow in a selective medium or are otherwise identifiable, for example, through fluorescence. In preferred embodiments, concomitant delivery of a reporter protein (e.g., Bla) to the host cell (e.g., *E. coli*) periplasm in a correctly folded orientation confers a resistant phenotype (e.g., ampicillin resistant phenotype) to cells. In some embodiments, growth of host cells correlates with the target protein being soluble and/or properly folded. In some embodiments, a target protein that is not soluble and/or that does not fold correctly does not confer resistance (e.g., ampicillin resistance) to host cells (e.g., *E. coli*) expressing the fusion protein. Thus, in some embodiments, lack of growth of host cells correlates with the target protein being insoluble or not properly folded. In some embodiments, the relative growth rate correlates with the relative correct folding of the reporter protein (e.g., Bla) activity). In some embodiments, the methods of the present invention detect intermediate ranges of solubility or folding.

Accordingly, the present invention provides cells, compositions, and methods for determining whether a host cell expresses a polypeptide of interest in a folded, partially folded, or incorrectly folded form in the periplasm of the host cell. In some embodiments, the present invention utilizes the Signal Recognition Particle-dependent (SRP-dependent) pathway to report protein folding and solubility in host cells (e.g. *E. coli*) (See, e.g., FIG. 1). In preferred embodiments, the present invention provides a fusion protein, and nucleic acids encoding the same, wherein the fusion protein comprises a signal peptide recognized by the SRP pathway, a target protein and a reporter protein (e.g., an antibiotic resistance marker such as beta-lactamase). In some embodiments, the fusion protein is inducible. In some embodiments, the fusion protein is constitutively expressed. Various nucleic acid constructs useful for expression of the fusion protein of the present invention are described below and in the Examples.

Fusion Proteins

An aspect of the present invention is the discovery that multiple peptides, polypeptides or proteins may be joined to a target protein (e.g., to create a fusion protein), wherein folding of the target protein is monitored by the growth, or lack of growth, of host cells comprising the fusion protein. The target protein may have the same length or amino acid sequence as the endogenously produced protein, if such protein exists. In other embodiments, the target protein may be a truncated protein, protein domain or protein fragment of a larger peptide chain. For example, the target protein may comprise a fragment of a membrane embedded or otherwise hydrophobic protein.

In some embodiments, fusion proteins are produced by operatively linking at least one nucleic acid encoding at least one amino acid sequence to at least a second nucleic acid encoding at least a second amino acid sequence, so that the encoded sequences are translated as a contiguous amino acid sequence either in vitro or in vivo. Fusion protein design and expression is well known in the art, and methods of fusion protein expression are described herein, and in references, such as, for example, U.S. Pat. No. 5,935,824, incorporated herein by reference in its entirety for all purposes. In some embodiments, linkers are used to join the various portions of the fusion protein. One such linker is another peptide, such as described in U.S. Pat. No. 5,990,275, incorporated herein by reference in its entirety for all purposes. In some embodiments, the fusion protein, and nucleic acids encoding the same, comprises a signal peptide recognized by the SRP-dependent pathway, a target protein and a reporter protein (e.g., an antibiotic resistance marker), wherein the signal sequence is N-terminal to the target protein that is N-terminal to the reporter protein (See, e.g., Example 1). However, it is contemplated that the portions of the fusion proteins may be assembled in any order (e.g., the target protein is to the N-terminus of the marker protein that is to the N-terminus of the signal peptide).

Signal Peptides

The present invention is not limited by the type of target protein assayed, nor to the type of SRP-dependent signal sequence or reporter protein used. Indeed, the present invention can be utilized characterize or monitor the solubility and/or folding of any protein, and the ability of other factors (e.g., small molecules, pharmaceuticals, etc.) to alter (e.g., enhance or inhibit) the solubility and/or folding of the target protein. The present invention is not limited to any particular SRP-dependent pathway signal peptide. Indeed, the use of variety of SRP-dependent pathway signal peptides are contemplated. A number of such sequences are known in the art, including those described in Huber et al., J. Bact. 187(9): 2983-91 (2005). Examples of SRP-dependent pathway signal sequences include, but are not limited to, DsbAss, TotTss, SfmCss, TolBss, Yralss, CcmHss, FocCss, NikAss, and FlgIss.

Proteins of interest

Studies conducted during the development of the present invention demonstrate that compositions and methods of the present invention reliably monitor protein solubility and/or folding across a range of biologically relevant target proteins (See, e.g., the Examples). For example, in some embodiments, a target protein may be a wild-type (e.g., full length) protein or may be a peptide fragment thereof (e.g., a polypeptide sequence of 4 or more amino acids, or preferably 10 or more amino acids). In some embodiments, the polypeptides are "heterologous," meaning that they are foreign to the host cell being utilized (e.g., a human protein produced by an E. coli cell, or a mammalian polypeptide produced by a yeast cell, or a human polypeptide produced from a human cell line that is not the native source of the polypeptide). Thus, the target protein may be any protein of interest for which the solubility and/or folding is to be analyzed. For example, the target protein may be Alzheimer's amyloid peptide (Aβ), SOD1, presenillin 1 and 2,αsynuclein, amyloid A, amyloid P, activin, anti-HER-2, bombesin, enkephalinase, protease inhibitors, therapeutic enzymes, α1-antitrypsin, mammalian trypsin inhibitor, mammalian pancreatic trypsin inhibitor, calcitonin, cardiac hypertrophy factor, cardiotrophins (such as cardiotrophin-1), CD proteins (such as CD-3, CD-4, CD-8and CD-19), CFTR, CTNF, DNase, human chorionic gonadotropin, mouse gonadotropin-associated peptide, cytokines, transthyretin, amylin, lipoproteins, lymphokines, lysozyme, a growth hormone (including human growth hormone), bovine growth hormone, growth hormone releasing factor, parathyroid hormone, thyroid stimulating hormone, growth factors, brain-derived neurotrophic growth factor, epidermal growth factor (EGF), fibroblast growth factor (such as α FGF and β FGF), insulin-like growth factor-I and -II, des(1-3)-IGF-I (brain IGF-I), insulin-like growth factor binding proteins, nerve growth factor (such as NGF-β), platelet-derived growth factor (PDGF), vascular endothelial growth factor (VEGF), receptors for growth hormones or growth factors, transforming growth factor (TGF) (such as TGF-α, TGF-β1, TGF-β2, TGF-β3, TGF-β4 or TGF-β5) neurotrophic factors (such as neurotrophin-3, -4,-5, or -6), gelsolin, glucagon, kallikreins, mullerian-inhibiting substance, neurotrophic factors, p53, protein A or D, prorelaxin, relaxin A-chain, relaxin B-chain, rheumatoid factors, rhodopsin, a serum albumin (such as human serum albumin), inhibin, insulin, insulin chains, insulin A-chain, insulin β-chain, insulin receptor, proinsulin, luteinizing hormone, integrin, interleukins (ILs) (such as IL-1 to IL-10, IL12, IL-13), erythropoietin, thrombopoietin, fibrillin, follicle stimulating hormone, clotting factors (such as factor VIIIC, factor IX, tissue factor, and von Willebrands factor, anti-clotting factors (such as Protein C, atrial naturietic factor, lung surfactant), a plasminogen activator (such as human tissue plasminogen activator or urokinase), thrombin, tumor necrosis, addressins, bone morphogenetic proteins (BMPs), collagen, colony stimulating factors (CSFs) (such as M-CSF, GM-CSF and G-CSF), decay accelerating factor, homing receptors, interferons (such as interferon-α, -βand -γ), keratin, osteoinductive factors, PRNP, regulatory proteins, superoxide dismutase, surface membrane proteins, transport proteins, T-cell receptors, viral antigens such as a portion of the AIDS envelope, immunoglobulin light chain, antibodies, antibody fragments (such as single-chain Fv fragment (scFv), single-chain antibody (scAb), $F_{AB}$ antibody fragment, diabody, triabody, fluorobody), antigens such as gp120(IIIb) immunotoxins, atrial natriuretic peptide, seminal vesicle exocrine protein, β2-microglobulin, PrP, precalcitonin, ataxin 1, ataxin 2, ataxin 3, ataxin 6, ataxin 7, huntingtin, androgen receptor, CREB-binding protein, gp120, p300, CREB, API, ras, NFAT, jun, fos, dentaorubral pallidoluysian atrophy-associated protein, a microbial protein (e.g., maltose binding protein, ABC transporter, glutathione S transferase, thioredoxin, β-lactamase), green fluorescent protein, red fluorescent protein, or derivatives or active fragments or genetic variants of any of the peptides listed above. The polypeptides may be native or mutated polypeptides, and preferred sources for such mammalian polypeptides include human, bovine, equine, porcine, lupine and rodent sources, with human proteins being particularly preferred.

Reporter proteins and selectable markers

In some embodiments, the reporter protein is all or a portion of a drug resistant marker (e.g., an antibiotic resistance protein). In some embodiments, the antibiotic resistant protein is encoded by all or a portion of the aada gene, the streptomycin phosphotransferase (SPT) gene, the neomycin phosphotransferase gene (NPTII), the hygromycin phosphotransferase (HPT) gene, or genes encoding resistance to ampicillin, tetracycline, or chloramphenicol. In some embodiments, the marker protein is an enzyme or a portion of an enzyme that can be readily assayed (such as alkaline phosphatase, β-galactosidase, β-glucoronidase, chloramphenicol acetyl transferase (CAT), DHFR, luciferase). In some embodiments, the marker protein is a fluorescent protein (such as green fluorescent protein (GFP), GFP-SsrA (See, e.g., DeLisa et al., 2002), yellow fluorescent protein (YFP), cyan fluorescent protein (CFP), blue fluorescent protein (BFP), red fluorescent protein (DsRed, mRFP) and genetic variants thereof). In preferred embodiments, the marker protein is mature TEM1β-lactamase protein (Bla). Because Bla confers antibiotic resistance on Gram-negative bacteria when present in the periplasmic space, it minimally acts to report the cellular localization of a protein chimera, not its solubility.

Fusion protein nucleic acids of the present invention may comprise additional sequences, such as coding sequences within the same transcription unit, controlling elements such as ribosome binding sites, and polyadenylation sites, additional transcription units under control of the same or a different promoter, sequences that permit cloning, expression, and transformation of a host cell, and any such construct as may be desirable to provide in embodiments of the invention.

The fusion protein nucleic acids may also include a polynucleotide sequence that encodes a molecular tag that can facilitate separation of a host cell that expresses the fusion protein from a host cell that does not express the fusion protein. For example, an epitope for an antibody can function as a molecular tag; cells that express the fusion protein can then be immobilized by contacting the cells with a solid support to which is attached antibodies that specifically recognize the epitope. Other suitable molecular tags are well known to those of skill in the art, and include, for example, a poly-histidine tag, or a FLAG peptide.

For example, in some embodiments, the fusion protein construct may comprise a nucleic acid sequence encoding a FlAsH binding motif (See, e.g., Example 7). The use of a FlAsH tag permits a greater range (e.g., nearly unlimited range) of potential attachment sites to a target protein (e.g., on the N-terminus, C-terminus or even embedded within the target protein—e.g., when C-terminal and/or N-terminal regions are being analyzed for the ability to interact with other proteins that may alter target protein solubility—e.g., chaperone proteins). The use of such tags enables one to identify a target protein from other proteins within a host cell.

Nucleic Acid Sequences and Vectors

The polynucleotides and sequences embodied in this invention can be obtained using, among other methods, chemical synthesis, recombinant cloning methods, PCR, or any combination thereof. PCR technology is the subject matter of U.S. Pat. Nos. 4,683,195; 4,800,159; 4,754,065; and 4,683,202 and described in PCR: THE POLYMERASE CHAIN REACTION (Mullis et al. eds, Birkhauser Press, Boston (1994)) and references cited therein. Alternatively, one of skill in the art can use the sequences provided herein, or available from other sources (e.g., ncbi.nlm.nih.gov) and a commercial DNA synthesizer, PCR, or other molecular biological techniques to synthesize or otherwise attain the nucleic acid sequence (e.g., DNA sequence) of any target protein of interest.

Once the target protein of interest, reporter protein and SRP-dependent pathway signal sequence are chosen, they may be operatively expressed in a recombinant vector. The vector may be expressed in vitro or in vivo for analyzing and/or altering target protein solubility and/or folding. As used herein, the term "vector" is used in reference to nucleic acid molecules that transfer nucleic acid (e.g., DNA) segment(s) from one cell to another. The term "vehicle" is sometimes used interchangeably with "vector." A nucleic acid sequence can be "exogenous" or "heterologous," which means that it is foreign to the cell into which the vector is being introduced or that the sequence is homologous to a sequence in the cell but in a position within the host cell nucleic acid in which the sequence is ordinarily not found. Vectors include, but are not limited to, plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1994, both incorporated herein by reference.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. In addition to control sequences that govern transcription and translation, vectors and expression vectors may contain nucleic acid sequences that serve other functions as well, some of which are described below.

In preferred embodiments, the vectors of the present invention comprise in 5' to 3' order or other operable order a SRP-dependent pathway signal sequence, a multiple cloning site, and a reporter protein sequence. In preferred embodiments, the protein of interest is inserted into the multiple cloning site. The sequence of the protein of interest can also be easily removed for cloning into other vectors for use in other assay of screening steps, such as iterative directed evolution procedures or use in other protein folding assays. In preferred embodiments, the vector is a plasmid containing additional elements useful expressing the fusion protein in a host cell, such as a preferred $E. coli$ strain. In further preferred embodiments, the vectors additional comprise one or more of the elements described below.

Promoters and Enhancers. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence (e.g., a nucleic acid sequence encoding a fusion protein of the present invention) to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," e.g., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (see U.S. Pat. No. 4,683,202, U.S. Pat. No. 5,928,906, each incorporated herein by reference). It is further contemplated that control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment (e.g., comprising nucleic acid encoding a fusion protein of the present invention) in the cell type, organelle, and organism chosen for expression. Those of skill in the art of microbiology and molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct the desired level expression of the introduced DNA segment comprising a target protein of the present invention (e.g., high levels of expression that are advantageous in the large-scale production of recombinant proteins and/or peptides). The promoter may be heterologous or endogenous.

Multiple elements/promoters may be employed in the context of the present invention to regulate the expression of nucleic acid encoding a fusion protein of the present invention. For example, the promoter/element may be, but is not limited to, lac, pho (e.g. phoA), tac, trc, trp, tet, araBAD, $\lambda P_L$ T3, T7, T7-lac and SP6. Furthermore, it is contemplated that any inducible or constitutively active promoter finds use in the present invention.

Initiation Signals and Internal Ribosome Binding Sites. A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

Multiple Cloning Sites. Vectors may include a multiple cloning site (MCS), which is a nucleic acid region that contains multiple restriction enzyme sites, any of which can be used in conjunction with standard recombinant technology to digest the vector. (See, e.g., Example 1, and Carbonelli et al., 1999, Levenson et al., 1998, and Cocea, 1997, incorporated herein by reference.). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant nucleic acid technology.

Splicing Sites. Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression.

Polyadenylation Signals. In expression, a polyadenylation signal may be included to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Origins of Replication. In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Selectable and Screenable Markers. In certain embodiments of the invention, in addition to the portion of the fusion protein, and nucleic acid sequences encoding the same, that contains a marker protein, a cell that contains a fusion protein nucleic acid construct of the present invention may be identified in vitro or in vivo by including a marker (e.g., either the same or different marker than that present in the fusion protein) in the expression vector. Such markers confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

The inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a fusion protein of the present invention. Further examples of selectable and screenable markers are well known to one of skill in the art.

Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. In some embodiments, a host cell is used as a recipient for vectors. A host cell may be "transfected" or "transformed," which refers to a process by which exogenous nucleic acid is transferred or introduced into the host cell. A transformed cell includes the primary subject cell and its progeny.

The fusion protein constructs, host cells and methods of the present invention are also useful for identifying variations in a process for biosynthesis of a target protein. The process can be varied to modify the solubility of the target protein. For example, a cell containing a fusion protein nucleic acid is cultured under alternative conditions and the growth of the host cells under selective conditions monitored. For example, protein solubility may be affected by the temperature, medium composition, or oxygen concentration in which the host cells are cultured. The method by which host cell growth is measured provides an immediate readout of solubility and permits a variety of alternative conditions to be tested with minimal effort, to identify those conditions where the highest proportion of soluble target protein is produced.

The constructs also are useful to compare alternative cells to identify a cell that synthesizes an increased amount of soluble target protein by performing a method identified herein with at least two alternative cells and comparing the amount of host cell growth to identify a cell that expresses an increased amount of soluble target protein.

As used herein, the terms "engineered" and "recombinant" cells or host cells are intended to refer to a cell into which an exogenous DNA segment or gene, such as a cDNA or gene encoding at least one fusion protein has been introduced. Therefore, engineered cells are distinguishable from naturally occurring cells which do not contain a recombinantly introduced exogenous DNA segment or gene. Engineered cells are thus cells having a gene or genes introduced through human intervention. Recombinant cells include those having an introduced cDNA or genomic gene, and also include genes positioned adjacent to a promoter not naturally associated with the particular introduced gene.

The invention is not limited to any particular host cell. A host cell may be prokaryotic or eukaryotic. In some embodiments, prokaryotic host cells are *E. coli* strain MC4100, B1LK0, RR1, *E. coli* LE392, *E. coli* B, *E. coli* X 1776 (ATCC No. 31537) as well as *E. coli* W3110 (F-, λ-, prototrophic, ATCC No. 273325); bacilli such as *Bacillus subtilis*; and other enterobacteriaceae such as *Salmonella typhimurium*, *Serratia marcescens*, and various *Pseudomonas* species. However, potential host cells are not limited to these examples. Indeed, a host cell may be any species of bacteria selected from the group consisting of *Acetobacter, Actinomyces, Aerobacter, Agribacterium, Azotobacter, Bacillus, Bacteroides, Bordetella, Brucella, Chlamydia, Clostridium, Corynebacterium, Erysipelothrix, Escherichia, Francisella, Fusobacterium, Haemophilus, Klebsiella, Lactobacillus, Listeria, Mycobacterium, Myxococcus, Neisseria, Nocardia, Pasteurella, Proteus, Pseudomonas, Rhizobium, Rickettsia, Salmonella, Serratia, Shigella, Spirilla, Spirillum, Staphylococcus, Streptococcus, Streptomyces, Trepanema, Vibrio, Vibrio,* and *Yersinia*. Alternatively, the host cells may be mammalian cells such as CHO cells.

With regard to the expression of fusion proteins of the present invention, once a suitable fusion protein nucleic acid encoding sequence has been obtained, one may proceed to prepare an expression system (e.g., expressing fusion protein constructs within host cells). The engineering of DNA segment(s) for expression in a prokaryotic or eukaryotic system may be performed by techniques generally known to those of skill in recombinant expression.

It is believed that virtually any expression system may be employed in the expression of the proteins of the present invention. Prokaryote- and/or eukaryote-based systems can be employed for use with the present invention to produce nucleic acid sequences, or their cognate polypeptides, proteins and peptides. Many such systems are commercially and widely available.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude or more larger than the cDNA gene. However, it is contemplated that a genomic version of a particular gene may be employed where desired.

It is contemplated that a fusion protein of the present invention (e.g., comprising a SRP-dependent pathway sequence, a target protein and a reporter protein) may be co-expressed with other selected proteins, polypeptides or peptides (e.g., protein chaperones, binding partners, and the like, or mutant forms thereof), wherein the proteins are co-expressed in the same cell or gene(s) may be provided to a cell that already has another selected protein. Co-expression may be achieved by co-transfecting the cell with two distinct recombinant vectors, each bearing a copy of either of the respective DNA. Alternatively, a single recombinant vector may be constructed to include the coding regions for each of the proteins of interest (e.g., a fusion protein and a chaperone) that can then be expressed in cells transfected with the single vector. In either event, the term "co-expression" herein refers to the expression of both at least one selected nucleic acid encoding one or more fusion proteins (e.g., comprising at least one or more target proteins) and at least a second selected nucleic acid or gene encoding at least one or more secondary selected proteins, polypeptides or peptides in the same recombinant cell.

While it is conceivable that a fusion protein may be delivered directly, a preferred embodiment involves introducing a nucleic acid encoding a fusion protein of the present invention to a cell. Following introduction into the host cell, the fusion protein is synthesized by the transcriptional and translational machinery of the cell. In some embodiments, additional components useful for transcription or translation may be provided by the expression construct comprising fusion protein nucleic acid sequence.

In some embodiments, the nucleic acid encoding the fusion protein may be stably integrated into the genome of the cell. In yet further embodiments, the nucleic acid may be stably maintained in the cell as a separate, episomal segment of DNA, such as a plasmid. Such nucleic acid segments or "episomes" encode sequences sufficient to permit maintenance and replication independent of or in synchronization with the host cell cycle. How the expression construct is delivered to a cell and where in the cell the nucleic acid remains is dependent on, among other things, the type of expression construct employed.

A number of procedures exist for the preparation of competent bacteria and the introduction of DNA into those bacteria. Protocols for the production of competent bacteria have been described (Hanahan (J. Mol. Biol. 166: 557-580 (1983); Liu et al., Bio Techniques 8:21-25 (1990); Kushner, In: Genetic Engineering: Proceedings of the International Symposium on Genetic Engineering, Elsevier, Amsterdam, pp. 17-23 (1978); Norgard et al., Gene 3:279-292 (1978); Jessee et al., U.S. Pat. No. 4,981,797); Maniatis et al., Molecular Cloning, A Laboratory Manual, Cold Spring Harbor Press, Cold Spring Harbor, N.Y. (1982).

Another rapid and simple method for introducing genetic material into bacteria is electroporation (Potter, Anal. Biochem. 174: 361-73 (1988)). This technique is based upon the original observation by Zimmerman et al., J. Membr. Biol. 67: 165-82 (1983), that high-voltage electric pulses can induce cell plasma membranes to fuse. Subsequently, it was found that when subjected to electric shock (typically a brief exposure to a voltage gradient of 4000-16000 V/cm), the bacteria take up exogenous DNA from the suspending solution, apparently through holes momentarily created in the plasma membrane. A proportion of these bacteria become stably transformed and can be selected if a suitable marker gene is carried on the transforming DNA (Newman et al., Mol. Gen. Genetics 197: 195-204 (1982)). With $E.$ $coli$, electroporation has been found to give plasmid transformation efficiencies of $10^9$-$10^{10}$ T/ug DNA (Dower et al., Nucleic Acids Res. 16: 6127-6145 (1988)).

Bacterial cells are also susceptible to transformation by liposomes (Old and Primrose, In: Principles of Gene Manipulation: An Introduction to Gene Manipulation, Blackwell Science (1995)). A simple transformation system has been developed which makes use of liposomes prepared from cationic lipid (Old and Primrose, In: Principles of Gene Manipulation: An Introduction to Gene Manipulation, Blackwell Science (1995)). Small unilamellar (single bilayer) vesicles are produced. DNA in solution spontaneously and efficiently complexes with these liposomes (in contrast to previously employed liposome encapsidation procedures involving nonionic lipids). The positively-charged liposomes not only complex with DNA, but also bind to bacteria and are efficient in transforming them, probably by fusion with the cells. The use of liposomes as a transformation or transfection system is called lipofection.

A number of procedures also exist for introducing nucleic constructs and vectors into mammalian cells. For example, calcium phosphate co-precipitation, electroporation and lipofection may also be used with mammalian cells. See, e.g., Potter et al., 1984; Graham and Van Der Eb, 1973; Chen and Okayama, 1987; Rippe et al., 1990; Graham et al., 1977; U.S. Pat. No. 5,670,488, incorporated herein by reference; Racher et al. (1995); Karlsson et al. (1986); Levrero et al., 1991; Gomez-Foix et al., 1992; U.S. Pat. No. 5,139,941 and U.S. Pat. No. 4,797,368, each incorporated herein by reference. Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

It is contemplated that proteins may be expressed in cell systems or grown in media that enhance protein production. One such system is described in U.S. Pat. No. 5,834,249, incorporated herein by reference in its entirety. In certain embodiments, the fusion protein may be co-expressed with one or more proteins that enhance refolding. Such proteins that enhance refolding include, for example, DsbA or DsbC proteins. A cell system co-expressing the DsbA or DsbC proteins are described in U.S. Pat. No. 5,639,635, incorporated herein by reference in its entirety. In certain embodiments, it is contemplated that a temperature sensitive expression vector may be used to aid assaying protein folding at lower or higher temperatures than many $E.$ $coli$ cell strain's optimum growth at about 37° C. For example, a temperature sensitive expression vectors and host cells that express proteins at or below 20° C. is described in U.S. Pat. Nos. 5,654,169 and 5,726,039, each incorporated herein by reference in their entireties.

Screening Systems

The present invention provides systems and methods for screening of host cells comprising libraries of variants of the same protein or different proteins. The use of selectable markers allows for the high throughput screening of such nucleic acid libraries. Accordingly, the present invention provides libraries of host cells, in which the cells of each population differ in the fusion protein expressed by the cells. For example, the fusion proteins can differ due to amino acid substitutions, deletions, or insertions in the target protein compared to a reference target protein amino acid sequence (e.g., an unmodified or wild type target protein sequence). Alternatively, the target proteins expressed by the populations of host cells can be different fragments of a larger polypeptide.

Accordingly, in some embodiments, the present invention provides methods for screening an expression library of clones to identify those clones that express soluble protein. This library can consist of alterations in the gene (or portion thereof) expressing the target protein (or portion thereof) of interest. Alterations of the gene can be provided by any of several widely used methods. These include, but are not limited to, making truncations in the gene, random chemical mutagenesis, random mutagenesis through erroneous nucleotide incorporation, or site-directed mutagenesis methods. This library of alterations can then be transformed into host cells. Individual clones of the transformed host cells are then cultured under conditions where the fusion protein containing a target protein, or altered form thereof, are expressed. The growth of the host cells in a selective environment (e.g., in the presence of ampicillin) can then be measured. Thus, host cell clones that are able to grow or that display increased growth (e.g., rate of growth) are identified that contain more soluble derivatives of the target protein. Likewise, if desired, clones that contain a less soluble form of the target protein can also be identified in host cell clones that fail to grow or that grow more slowly.

The present invention also provides methods for screening for mutations in a host cell, or in a target protein sequence, that improve the solubility of a target protein. For example, cells comprising a fusion protein of the present invention can be treated with a mutagen, and those host cells that display an increase in growth (e.g., rate or abundance) in the presence of a selective marker (e.g., ampicillin) identified. A "mutagen" is intended to include, but not be limited to chemical mutagens such as ethyl methane sulphonate, N-methyl-N'-nitroso-guanidine and nitrous acid as well as physical agents such as ionizing radiation.

In an alternative embodiment, mutations can be introduced into a polynucleotide sequence encoding a target protein. The altered polynucleotide is then tested to determine whether the solubility of the target protein is changed (e.g., as monitored by growth in a selective environment, e.g., in the presence of ampicillin). Such mutations include, but are not limited to, mutations induced by a mutagen; site directed mutations that alter specific amino acid residues such as mutation of cysteine residues to eliminate disulfide bonds; deletions that remove sets of specific amino acids such as deletion of a continuous stretch of hydrophobic amino acids; and fusions of the target protein to a second, particularly soluble protein. In each case, the solubility of the target protein is assessed by determining growth of the host cells in a selective environment.

Accordingly, the present invention provides methods where mutations are introduced into the nucleic acid sequences of one or more proteins of interest to provides a library of variant or mutagenized target nucleic acid sequences. In some embodiments, directed evolution procedures are used to prepare libraries of nucleic acid sequences in which a target protein of interest has been mutagenized. The mutagenized nucleic acid sequences are preferably cloned into vectors of the present invention between a SPR-dependent pathway signal sequence and a reporter protein sequence. The vectors are then introduced into host cells to provide a library of host cells comprising the nucleic acid sequences of interest. The host cells are then cultured under selective conditions, for example, in the presence of an antibiotic. Host cells that express target protein variants that are exported to the periplasm and correctly folded in the periplasm are resistant to the selection employed and grow. Clones of the host cells that survive the selection are identified and grown. The mutagenized target protein of interest can then be identified, for example, by subcloning and subsequent sequencing or just by sequencing.

In some embodiments, variants may be produced by methods such as directed evolution or other techniques for producing combinatorial libraries of variants. The synthesis of degenerate oligonucleotides is well known in the art (See e.g., Narang, Tetrahedron Lett., 39:39 (1983); Itakura et al., Recombinant DNA, in Walton (ed.), Proceedings of the 3rd Cleveland Symposium on Macromolecules, Elsevier, Amsterdam, pp 273-289 (1981); Itakura et al., Annu. Rev. Biochem., 53:323 (1984); Itakura et al., Science 198:1056 (1984); Ike et al., Nucl. Acid Res., 11:477 (1983), herein incorporated by reference in their entireties). Such techniques have been employed in the directed evolution of proteins (See e.g., Scott et al., Science 249:386 (1980); Roberts et al., Proc. Natl. Acad. Sci. USA 89:2429 (1992); Devlin et al., Science 249: 404 (1990); Cwirla et al., Proc. Natl. Acad. Sci. USA 87: 6378 (1990); each of which is herein incorporated by reference; as well as U.S. Pat. Nos. 5,223,409, 5,198,346, and 5,096,815; each of which is incorporated herein by reference). In some preferred embodiments, error prone PCR is used to introduce mutations into the nucleic acid sequence of the target protein of interest.

In some embodiments, the methods described above are used to prescreen large combinatorial libraries of proteins. Accordingly, the screening methods of the present invention may be combined with other screening methods, for example, a protein folding screen of the present invention may precede or be interspersed with other screening steps, such as iterative rounds of directed evolution as described in the patents and publications referenced above. In these methods, variants that fold correctly can be removed from the library prior to further screening to decrease the number of clones or variants that need to be screened. In other embodiments, the protein folding screening methods of the present invention are used in combination with other protein folding screens, such as those described in co-pending application Ser. No. 11/194,635, filed Aug. 1, 2005, incorporated by reference herein in its entirety.

The present invention also contemplates the use of other methods of introducing mutations into nucleic acid sequences. Chemical mutagenesis offers certain advantages, such as the ability to find a full range of mutant alleles with degrees of phenotypic severity, and is facile and inexpensive to perform. The majority of chemical carcinogens produce mutations in DNA. Benzo(a)pyrene, N-acetoxy-2-acetyl aminofluorene and aflotoxin B1 cause GC to TA transversions in bacteria and mammalian cells. Benzo(a)pyrene also can produce base substitutions such as AT to TA. N-nitroso compounds produce GC to AT transitions. Alkylation of the O4 position of thymine induced by exposure to n-nitrosourea results in TA to CG transitions.

Another useful mutagenesis technique is alanine scanning mutagenesis in which a number of residues are substituted individually with the amino acid alanine so that the effects of losing side-chain interactions can be determined, while minimizing the risk of large-scale perturbations in protein conformation.

In recent years, techniques for estimating the equilibrium constant for ligand binding using minuscule amounts of protein have been developed (See, e.g., U.S. Pat. Nos. 5,221,605 and 5,238,808, herein incorporated by reference in their entireties). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

Another method for generating libraries of polypeptides is described in U.S. Pat. No. 5,380,721, herein incorporated by reference in its entirety. The method comprises obtaining polynucleotide library members, pooling and fragmenting the polynucleotides, and reforming fragments therefrom, performing PCR amplification, thereby homologous recombining the fragments to form a shuffled pool of recombined polynucleotides.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. For example, a primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Zeng et al., 1996; Yelton et al., 1995; Hilton et al., 1996). Hundreds, and possibly even thousands, of site specific mutants must be studied. However, improved techniques make production and rapid screening of mutants much more straightforward. See, U.S. Pat. Nos. 5,798,208 and 5,830,650, herein incorporated by reference in their entireties, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166, herein incorporated by reference in their entireties.

Drug Discovery

Compositions and methods of the present invention also find use in the discovery of drugs that modulate the solubility and/or folding of proteins (e.g., disease related proteins). For example, the search for pharmaceuticals has focused on the identification of compounds that inhibit cellular processes. However, the increasing prevalence of diseases associated with protein misfolding such as Huntington's disease, Alzheimer's disease, Parkinson's disease, cystic fibrosis, amyotropic lateral schlerosis, Creutzfeld-Jacob disease, and some forms of diabetes and cancer presents a new challenge for the pharmaceutical industry. Thus, the present invention provides compositions and methods for use in screening and assaying protein folding related to these, and other diseases. For example, using the compositions and methods of the present invention, small molecules or other types of agents (pharmaceutical agents) may be identified that stabilizes the folding of a mutant protein involved in disease (e.g., p53). It will be apparent to those skilled in the art that this, and other, aspects of the present invention are easily amenable to a high-throughput procedure to rapidly screen a large number of alternative small molecules or agents (e.g., from a library of such materials). In some embodiments, these methods provide for the development of automated procedures for screening of the small molecules or agents. Thus, the present invention provides incredible savings in time and resources necessary for analyzing the solubility of proteins and materials (e.g., small molecules or agents) useful for altering the same.

Additionally, the compositions and methods of the present invention may be used to identify small molecules or other types of agents (pharmaceutical agents) that can be used to destabilize protein folding (e.g., cause aggregates). In some embodiments, the present invention provides methods for identifying an antibiotic agent.

For example, in some embodiments, the growth of host cells comprising a fusion protein (e.g., comprising a target protein of interest) contacted with a candidate agent (e.g., a candidate drug, pharmaceutical, small molecule or compound) is compared to growth of host cells comprising the fusion protein that is not contacted with the candidate agent. A decrease in growth of the host cells contacted with the candidate agent is indicative of a candidate agent that inhibits protein folding in the cell. In some embodiments, the growth of the host cells, whether or not a candidate agent (e.g., drug or antibiotic agent) is being tested, is under a selective pressure (e.g., exposed to a drug, antibiotic or other selective means).

As used herein, a "candidate agent" may be any agent that potentially inhibits or enhances protein folding and/or solubility, including, but not limited to, a drug, a pharmaceutical, a small molecule, and an compound. For example, the candidate agent may be a protein or fragment thereof, a small molecule, a chemical, or even a nucleic acid molecule. Using lead compounds to help develop improved compounds is known as "rational drug design" and includes not only comparisons with no inhibitors and enhancers of protein folding/solubility, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, it is possible to generate a three-dimensional structure for a target molecule, or a fragment thereof. This could be accomplished by x-ray crystallography, computer modeling or by a combination of both approaches.

It also is possible to use antibodies to ascertain the structure of a candidate enhancer or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful candidate agents. Screening of such libraries, including combinatorially generated libraries (e.g., peptide libraries), is a rapid and efficient way to screen large number of related (and unrelated) agents for activity. Combinatorial approaches also lend themselves to rapid evolution of potential drugs by the creation of second, third and fourth generation compounds modeled of active, but otherwise undesirable compounds.

Candidate agents may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the agents (e.g., pharmaceuticals) to be screened could also be derived or synthesized from chemical compositions or man-made compounds. Thus, it is understood that the candidate agent identified by the present invention may be any peptide, polypeptide, polynucleotide, small molecule inhibitors or any other chemicals or compounds (e.g., that may be designed through rational drug design starting from known inhibitors or enhancers).

Other potential agents include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating agents (e.g., compounds) initially identified, other sterically similar compounds may be formulated to mimic the key portions of the structure of the modulators. Such agents (e.g., compounds), which may include peptidomimetics of peptide modulators, may be used in the same manner as the initial modulators.

The invention also provides gene delivery vehicles and expression vectors and host or genetically modified cells containing at least polynucleotides of the invention and/or a fusion protein of the invention.

The present invention also provides gene delivery vehicles suitable for delivery and/or expression of a polynucleotide sequence (e.g., a nucleic acid sequence encoding a fusion protein of the present invention) of the invention into cells (whether in vivo, ex vivo, or in vitro). A polynucleotide sequence of the invention can be contained within a cloning or expression vector. These vectors (especially expression vectors) can in turn be manipulated to assume any of a number of forms which may, for example, facilitate delivery to and/or entry into a cell. Examples of suitable expression and delivery vehicles are provided elsewhere herein.

EXPERIMENTAL

The following examples are provided in order to demonstrate and further illustrate certain preferred embodiments and aspects of the present invention and are not to be construed as limiting the scope thereof.

Materials and Methods

Strains and plasmids. Redox-toggled experiments were performed in DHB4 E. coli cells (F' lacI$^q$pro/λ-ΔlacX74galK thi rpsL phoR ΔphoA(PvuII) ΔmalF3) or an isogenic derivative of DHB4, namely DHA, that carries the dsbA::kan allele. DeLisa, M.P., Tullman, D. & Georgiou, G. Folding quality control in the export of proteins by the bacterial twin-arginine translocation pathway. Proc Natl Acad Sci U S A 100, 6115-6120 (2003). All other experiments were performed in DH5α cells. Cloning was performed using standard molecular biological techniques and protocols. Sambrook, J. & Russell, D.W. Molecular cloning : a laboratory manual, Edn. 3rd. (Cold Spring Harbor Laboratory Press, Cold Spring Harbor, N.Y.; 2001). Plasmid pDMB (Fig. 1a) was constructed by inserting DNA for the DsbA signal peptide (ssDsbA; DNA bases 1-57 of the E. coli dsbA gene) between SacI and XbaI sites of pTrc99A-Cm. Fisher, A.C., Kim, W. & DeLisa, M.P. Genetic selection for protein solubility enabled by the folding quality control feature of the twin-arginine translocation pathway. Protein Sci 15, 449-458 (2006). Next, TEM 1-β-lactamase was inserted between the BamHI and HindIII sites. Finally, genes encoding POIs were inserted between the XbaI and SalI sites resulting in a sandwich fusion with the DNA encoding ssDsbA and TEM1-β-lactamase. The POIs included: MetF, MetK, GST, PhoA and TrxA, all of which were amplified from the E. coli genome using colony PCR; maltose binding proteins MalE, MalE31, MalE-G32D and MalE-133P[27] and single-chain antibodies scFv13 and scFv13-R4, which were kindly provided by J.-M. Betton; wildtype Aβ42 peptide and solubility-enhanced Aβ42 variants GM7, GM11, and GM6, which were kindly provided by M.H. Hecht; and GFP, which was PCR-amplified from pTMB-GFP. Martineau, P., Jones, P. & Winter, G. Expression of an antibody fragment at high levels in the bacterial cytoplasm. J Mol Biol 280, 117-127 (1998); Wurth, C., Guimard, N.K. & Hecht, M.H. Mutations that reduce aggregation of the Alzheimer's Abeta42 peptide: an unbiased search for the sequence determinants of Abeta amyloidogenesis. J Mol Biol 319, 1279-1290 (2002); Fisher et al., supra. Plasmid pTMB is identical to pDMB except that it contains the signal peptide of TorA (ssTorA; DNA bases 1-126 of the E. coli torA gene) between SacI and XbaI sites. Genes encoding the periplasmic chaperones SurA, FkpA, and Skp were PCR-amplified from E. coli genomic DNA and inserted between the NcoI and SalI sites of pBAD18-Kan, which is resistant to kanamycin and inducible by addition of arabinose and repressed by glucose. Guzman, L.M., Belin, D., Carson, M.J. & Beckwith, J. Tight regulation, modulation, and high-level expression by vectors containing the arabinose PBAD promoter. J Bacteriol 177, 4121-4130 (1995). All plasmids constructed in this study were confirmed by DNA sequencing.

Expression of fusion proteins and cell growth assays. Cells carrying a folding reporter plasmid were grown overnight at 37° C. in LB medium containing 50 µg/mL chloramphenicol (Cm). Screening of cells on LB agar was performed by first normalizing overnight cultures by $OD_{600}$ and then spotting 5 µL of serially-diluted (10-10$^5$-fold) cells on LB agar plates containing 100 µg/mL ampicillin (Amp) or 20 µg/mL Cm. LB agar plates used to determine the effectiveness of periplasmic chaperone overexpression were supplemented with 50 µg/mL kanamycin (Kan), along with either 20 µg/mL Cm or 200 µg/mL Amp and either 0.2% arabinose or 0.2% glucose. In all cases, the plates were incubated 16 h at 37° C. and then photographed using a ChemiDoc Imaging System (BioRad).

MIC/MBC determination. Approximately 200 colony forming units (CFUs) of each clone were plated on LB agar plates containing 0, 3, 6, 12, 25, 50, 100, 200, 400, 800, or 1600 µg/mL Amp or 20 µg/mL Cm. Growth inhibition (MIC) was observed as the minimum concentration of Amp on which colony size was significantly smaller than control. The inability to grow on Amp (MBC) was determined as the minimum concentration at which no colonies appeared on the plates.

Protein analysis. Cells were grown overnight at 37° C. in flasks containing 50 ml LB media with appropriate antibiotics. An equivalent number of cells was subjected to subcellular fractionation into soluble cytoplasmic and periplasmic fractions using the ice-cold osmotic shock procedure. Delisa et al., 2003, supra. Western blotting of these fractions was performed as previously described using either 10 µg/mL anti-β-lactamase antibodies (AbCam) or anti-DsbA serum diluted 1:5,000 (kindly provided by J. C. Bardwell) as the primary antibody and either anti-mouse or anti-rabbit horseradish peroxidase conjugate diluted 1:2,500 (Promega, Madison, Wis.) as the secondary antibody. Delisa et al., 2003, supra. Bands were visualized via chemiluminescent substrate (Bio-Rad) on Kodak film. The quality of all fractionations was determined by immunodetection of the cytoplasmic GroEL protein. Fractions from GFP-expressing cells were assayed for fluorescence by loading 100-µL portions into 96-well plates and quantifying the GFP activity (ex: 488 nm; em: 509 nm) using a microplate reader (Synergy HT, BioTek Instruments). Finally, soluble fractions were assayed for Bla activity based on nitrocefin (50 µM) hydrolysis in 96-well format as described. Galarneau, A., Primeau, M., Trudeau, L. E. & Michnick, S. W. Beta-lactamase protein fragment complementation assays as in vivo and in vitro sensors of protein-protein interactions. Nat Biotechnol 20, 619-622 (2002). All fluorescence and Bla activity measurements were performed in triplicate.

Library creation and selection of clones. A library of Aβ42 sequences was created according to Fisher et al., supra, except that the plasmid backbone was pDMB. Briefly, error-prone PCR was performed on the gene encoding the Aβ42 peptide. The library was cloned between the XbaI and SalI sites of pDMB and estimated to contain ~50,000 members. Selection was performed by plating ~2,000 CFUs per plate on 25 µg/mL Amp. To eliminate false positives (e.g., small in-frame fragments that confer higher-than-expected resistance to Amp), clones growing on 25 µg/mL Amp were inoculated in 96-well cultures and replica spot-plated as above at $10^3$ dilution on 25 and 100 µg/mL Amp. Only those clones that grew on 25 µg/mL Amp but failed to grow on 100 µg/mL Amp were sequenced and characterized by MIC/MBC determination.

EXAMPLE 1

An Engineered Assay for Folding and Solubility in the Periplasm

We hypothesized that periplasmic export of a chimeric protein comprised of a POI fused to TEM-1 Bla would allow intimate coupling between Bla activity and the folding and solubility of a fused POI in the periplasm. Steiner, D., Forrer, P., Stumpp, M. T. & Pluckthun, A. Signal sequences directing cotranslational translocation expand the range of proteins amenable to phage display. *Nat Biotechnol* 24, 823-831 (2006). To test this notion, we created a tripartite gene fusion of ssDsbA-POI-Bla in plasmid pDMB (FIG. 1a). We chose ssDsbA because it has been shown to direct co-translational export of heterologous proteins through the SRP-dependent secretory pathway. By virtue of this unique protein routing mechanism, POIs would be expected to experience only minimal (if any) residence time in the cytoplasm, thereby ensuring that folding takes place predominantly in the periplasmic space. TEM-1 Bla was chosen as the reporter because it readily confers an Amp-resistant phenotype provided that it is localized in the periplasm in a correctly folded conformation (FIG. 1b). Thus, if the POI attains a folded conformation, it will allow its C-terminal fusion partner, Bla, to be folded and active in the periplasm; if the POI does not stably fold, the POI-Bla fusion will be subject to cellular quality control (e.g., aggregation, deposition in periplasmic inclusion bodies and/or degradation by proteases) and consequently Bla will be inactive. In this study, a variety of different POIs were cloned into pDMB and characterized based on their Amp-resistant phenotype.

EXAMPLE 2

Modulating the Periplasmic Redox State Affects Folding

One of the hallmarks of the bacterial periplasmic environment is its ability to catalyze the formation of disulfide bonds, an important and often essential part of the native structure for numerous proteins. Steiner, D., Forrer, P., Stumpp, M.T. & Pluckthun, A. Signal sequences directing cotranslational translocation expand the range of proteins amenable to phage display. Nat Biotechnol 24, 823-831 (2006); DeLisa, M.P., Samuelson, P., Palmer, T. & Georgiou, G. Genetic analysis of the twin arginine translocator secretion pathway in bacteria. J Biol Chem 277, 29825-29831 (2002); Sone, M., Kishigami, S., Yoshihisa, T. & Ito, K. Roles of disulfide bonds in bacterial alkaline phosphatase. J Biol Chem 272, 6174-6178 (1997). To determine the effectiveness of our system as a reporter of periplasmic folding, we investigated *E. coli* alkaline phosphatase (PhoA) because this enzyme requires two disulfide bonds in order to attain a stable and catalytically active conformation[34]. As expected, expression of ssDsbA-PhoA-Bla in wildtype DHB4 cells conferred resistance to 100 µg/ml Amp (FIG. 1c). However, when the same construct was expressed in DHA cells that lacked the primary periplasmic oxidant DsbA that is essential for PhoA folding, resistance to this level of Amp was abolished. In fact, DHB4 cells expressing the ssDsbA-PhoA-Bla fusion exhibited a 33- and 16-fold higher MBC and MIC, respectively, than DHA cells expressing the same fusion (Table 1). Plating of the above cells on non-selective LB agar containing 50 µg/ml Cm revealed no measurable difference in cell growth (FIG. 1c), confirming that the difference in Amp resistance was specific to the folding of PhoA-Bla in the periplasm. To confirm that this difference was not attributable to redox-dependent changes in the folding of the Bla moiety itself, cells expressing ssDsbA fused directly to Bla without an intervening POI gene were plated on Amp. Consistent with earlier findings, the periplasmic redox state did not affect the folding or catalytic activity of Bla as evidenced by the identical growth phenotypes of DHB4 and DHA cells expressing ssDsbA-Bla on 100 µg/ml Amp (FIG. 1c) and as determined by MIC/MBC measurements (Table 1). Frech, C., Wunderlich, M., Glockshuber, R. & Schmid, F.X. Competition between DsbA-mediated oxidation and conformational folding of RTEM1 beta-lactamase. Biochemistry 35, 11386-11395 (1996).

TABLE 1

MIC and MBC of proteins of interest.

| Protein of Interest | strain | MIC (µg/ml) | MBC (µg/ml) |
|---|---|---|---|
| Alkaline Phosphatase (22 C.) | | | |
| PhoA | DHB4 | 50 | 100 |
| PhoA | DHA | 3 | 3 |
| ssTorA-PhoA-Bla | DHB4 | 6 | 6 |
| ssTorA-PhoA-Bla | DHA | 6 | 12 |
| ssDsbA-Bla | DHB4 | 1600 | 3200 |
| ssDsbA-Bla | DHA | 1600 | 3200 |
| scFv13 | | | |
| scFv13 | DHB4 | 200 | 400 |
| scFv13 | DHA | 50 | 50 |
| scFv13-R4 | DHB4 | 400 | 400 |
| scFv13-R4 | DHA | 50 | 100 |
| Maltose Binding proteins | | | |
| MalE wt | DH5α | 200 | 250 |
| G32D | DH5α | 175 | 200 |
| I33P | DH5α | 175 | 200 |
| MalE31 | DH5α | 175 | 175 |
| GroEL Substrates | | | |
| MetF | DH5α | 25 | 25 |
| MetK | DH5α | 3 | 6 |
| Amyloid β peptides | | | |
| Aβ42 | DH5α | 12 | 12 |
| A2* | DH5α | 25 | 25 |
| A4* | DH5α | 25 | 25 |
| B12* | DH5α | 25 | 25 |
| B9* | DH5α | 25 | 25 |
| H2* | DH5α | 25 | 50 |
| GM11 | DH5α | 50 | 100 |
| GM7 | DH5α | 50 | 100 |
| GM6 | DH5α | 100 | 100 |

Unless otherwise indicated, protein of interest is a fusion of ssDsbA-POI-Bla. Approximately 500 cfu were plated overnight at 37 C., except in the case of PhoA, which was plated at 22 C.
(*proteins engineered in this study)

Thus, the difference in Amp resistance seen for DHB4 and DHA cells expressing ssDsbA-PhoA-Bla is best explained by the fact that the periplasm of DHA cells is highly reducing and thus strongly disfavors the oxidation of protein thiols such as those required for PhoA folding. As a result, periplasmic PhoA-Bla is misfolded and unable to efficiently hydrolyze Amp. For comparison, DHB4 cells expressing ssTorA-PhoA-Bla were not resistant to 100 µg/ml (FIG. 1c). This is because the TorA signal peptide targets proteins to the bacterial Tat pathway, which requires that protein substrates fold in the cytoplasm prior to transport across the inner membrane. Delisa et al., 2003, supra. Since the cytoplasm of DHB4 cells is a reducing environment that precludes the formation of disulfide bonds in PhoA, transport of the ssTorA-PhoA-Bla fusion does not occur and as a result cells are sensitive to Amp.

To determine whether the ability to report redox-dependent folding was a general feature of our assay, we next analyzed the behavior of a single-chain antibody fragment specific for β-galactosidase (scFv13). Like PhoA, scFv13 folding is dependent on the formation of two intradomain disulfide bonds; in the absence of these bonds the fragment is unstable and expressed at very low levels. Martineau et al., supra. Similar to what was seen above, DHB4 cells expressing ssDsbA-scFv13-Bla were resistant to 100 µg/ml Amp whereas dsbA::kan cells were not (FIG. 1d). In fact, an approximate 8- and 4-fold difference in MBC and MIC, respectively, was observed for wildtype versus dsbA::kan cells (Table 1). To confirm that this observation was due to differences in folding behavior, Western blotting was performed on the soluble cytoplasmic and periplasmic fractions of DHB4 and DHA cells expressing ssDsbA-scFv13-Bl a. Consistent with these growth phenotypes, strong expression was detected predominantly in the periplasmic fraction of DHB4 cells, while virtually no cross-reacting bands were detected in any fraction isolated from DHA cells (Fig. 1e) confirming that scFv13 stability is dependent on disulfide bond formation. It is also noteworthy that scFv13-Bla localization was nearly 100% efficient, supporting our hypothesis that proteins targeted to the SRP pathway have a very short residence time in the cytoplasm. We also tested scFv13-R4, a variant of scFv13 engineered to have greater solubility under reducing conditions. In DHA cells, scFv13-R4 showed a two-fold increase in MBC over wildtype (Table 1), though in DHB4 cells, scFv13-R4 showed 4- and 8-fold higher MIC and MBC than the DHA cells. This implies that while scFv13-R4 shows increased solubility under reducing conditions, the protein is still not as soluble as it is when proper disulfide bonding occurs, in close agreement with in vitro folding data for this protein. Martineau et al., supra.

EXAMPLE 3

Probing intrinsic and extrinsic factors affecting periplasmic protein folding

Figure 2:
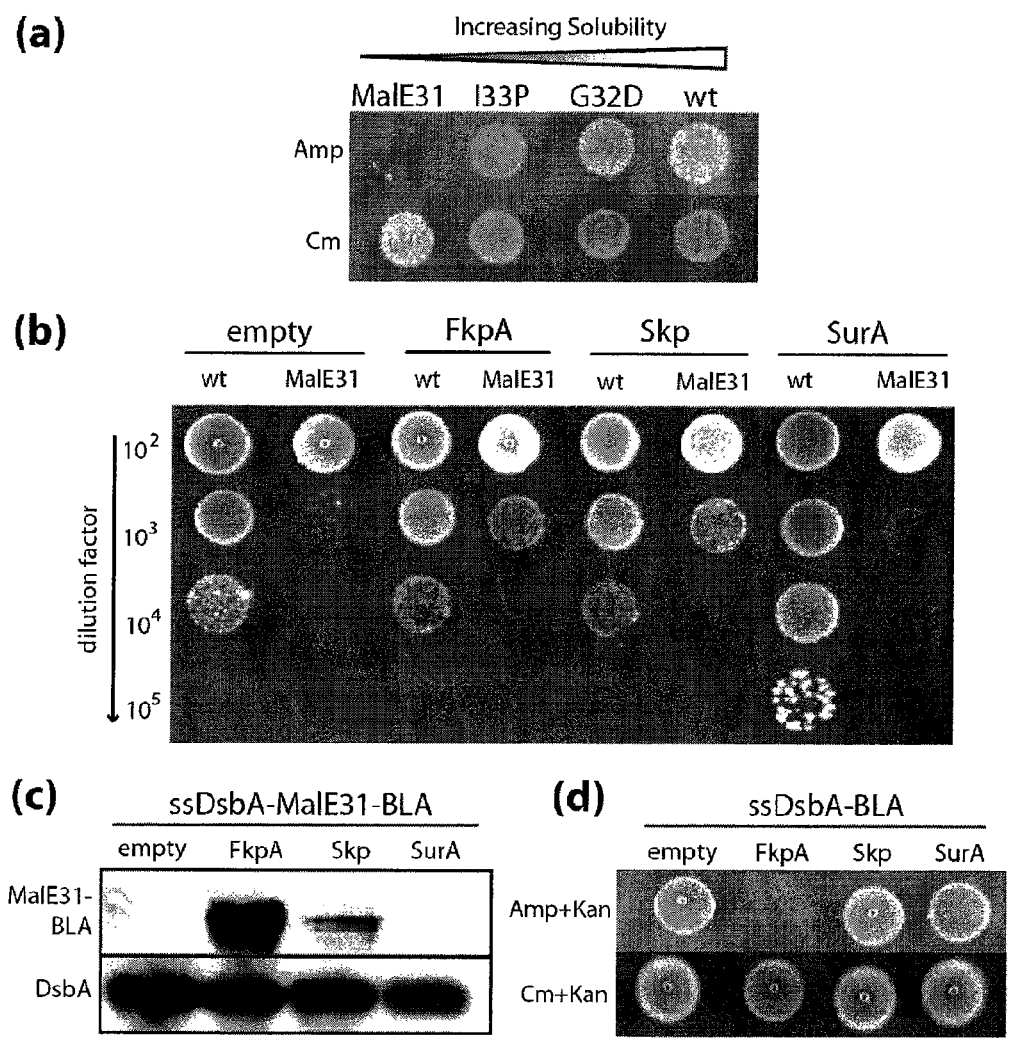
FIG. 2. Maltose binding proteins with varying solubilities. (a) DH5α cells expressing pDMB fusions to maltose binding protein variants MalE31, I33P, G32D, and wildtype MalE were spot plated on 100 µg/ml ampicillin or 50 µg/ml chloramphenicol as in FIG. 1c, except at a dilution factor of 10³ from overnight cultures. (b) Vector pBAD18-Kan expressing periplasmic chaperones FkpA, Skp, and SurA, along with empty pBAD18-Kan were transfected into cells expressing MalE wildtype (wt) and MalE31 fusions, then spot plated as in FIG. 1c at various dilution factors and at 200 µg/ml ampicillin and 50 µg/ml kanamycin. (c) Western blotting of cells expressing periplasmic chaperones as above and pDMB-MalE31, blotting with anti-Bla serum. The fractions were normalized by blotting with anti-DsbA serum since DsbA is a standard periplasmic protein. (d) Cells expressing ssDsbA-BLA were spot plated as in FIG. 1c on 50 µg/ml kanamycin and either 800 µg/ml ampicillin or 20 µg/ml Cm.

The wildtype E. coli maltose binding protein (MBP) is known to be soluble in the periplasm. In fact, it has been used in many cases as a fusion partner to aid expression of less-soluble proteins in cells. Kapust, R.B. & Waugh, D.S. Escherichia coli maltose-binding protein is uncommonly effective at promoting the solubility of polypeptides to which it is fused. Protein Sci 8, 1668-1674 (1999). However, Betton and co-workers have isolated point mutations that cause the protein to become kinetically trapped in off-pathway intermediates which are prone to aggregation. Arie, J.P., Miot, M., Sassoon, N. & Betton, J.M. Formation of active inclusion bodies in the periplasm of Escherichia coli. Mol Microbiol 62, 427-437 (2006). A double mutant containing substitutions at residues 32 and 33 of mature MBP, called MalE31, has been shown to form inclusion bodies when expressed in the periplasm. Betton, J.M. & Hofnung, M. Folding of a mutant maltose-binding protein of Escherichia coli which forms inclusion bodies. J Biol Chem 271, 8046-8052 (1996). To determine whether changes in the aggregation potential of misfolded proteins could be detected in our system, we tested four different variants of MBP: wildtype, G32D, I33P, and MalE31 by cloning the genes encoding these proteins into pDMB and evaluating their ability to confer resistance to cells. When dilutions of overnight cultures were plated on Amp, fusions to wildtype MBP but not MalE31 conferred strong resistance to cells grown on 100 µg/ml Amp (FIG. 2a). The measured MBC for the wildtype MBP fusion was 42% greater compared to the MalE31 fusion (Table 1). Importantly, cells grown on Cm showed no difference in growth phenotype. It is noteworthy that while there indeed exists a difference in Amp resistance, MalE31 fusions were capable of some in vivo Bla activity. This is in agreement with recent findings from Arié and colleagues showing that fusions of MalE31 to Bla retain some catalytic activity and with data from our Tat-based folding assay that MBP variants exhibit measurable solubility in the cytoplasm, albeit at a reduced level compared to wildtype MBP. Arie, J.P., Miot, M., Sassoon, N. & Betton, J.M. Formation of active inclusion bodies in the periplasm of Escherichia coli. Mol Microbiol 62, 427-437 (2006).

Previous studies have shown that upregulating periplasmic chaperone activity can decrease in vivo aggregation of MalE31. Arie, J. P., Sassoon, N. & Betton, J. M. Chaperone function of FkpA, a heat shock prolyl isomerase, in the periplasm of *Escherichia coli*. *Mol Microbiol* 39, 199-210 (2001). In this study, the periplasmic chaperone FkpA was found to decrease aggregation of MalE31, while another periplasmic chaperone SurA was not found to affect MalE31 aggregation. A third periplasmic chaperone called Skp is known for its ability to interact with a broad range of substrates and has been used to improve expression of phage-displayed proteins. Missiakas, D., Betton, J. M. & Raina, S. New components of protein folding in extracytoplasmic compartments of *Escherichia coli* SurA, FkpA and Skp/OmpH. *Mol Microbiol* 21, 871-884 (1996); Bothmann, H. & Pluckthun, A. Selection for a periplasmic factor improving phage display and functional periplasmic expression. *Nat Biotechnol* 16, 376-380 (1998). Based on these data, we reasoned that a chaperone-mediated decrease in MalE31 aggregation would lead to increased Bla activity in our assay. To test this hypothesis, we created plasmids expressing periplasmic chaperones FkpA, SurA, and Skp and co-transformed these plasmids into cells expressing wildtype MBP and MalE31 fusions. Spot-plating on Amp revealed a measurable difference in growth phenotype for the cases of FkpA and Skp co-expression with respect to the empty vector control, whereas co-expression of SurA showed no measurable difference compared to the control (FIG. 2b). Again, Cm control plates showed no growth difference across all cells (data not shown). To verify the solubility of the MalE31 fusions in the presence or absence of chaperones, Western blotting of periplasmic fractions from overnight cultures co-expressing the MalE31-Bla fusion along with either FkpA, Skp, SurA, or empty pBAD18-Kan vector was performed. FkpA and Skp co-expression resulted in increased solubility of the fusion, while SurA co-expression had no effect relative to the empty vector (FIG. 2c). Finally, to show that improvement in Bla activity resulted from an increase in MalE31 solubility and not by improved folding of the Bla domain itself, we tested ssDsbA-Bla fusions that lacked the MBP insertions. Amp resistance with respect to the control was similar in the case of Skp and SurA, but surprisingly decreased in the presence of FkpA (FIG. 2d) for reasons that are currently unclear. Nonetheless, Bla activity in itself was not significantly increased by the presence of any periplasmic chaperones. Incidentally, we found that co-expression of SurA increased the solubility of the fusion containing wildtype MBP (FIG. 2b) suggesting that SurA has specificity for wildtype MBP but not the MalE31 variant.

Figure 3:
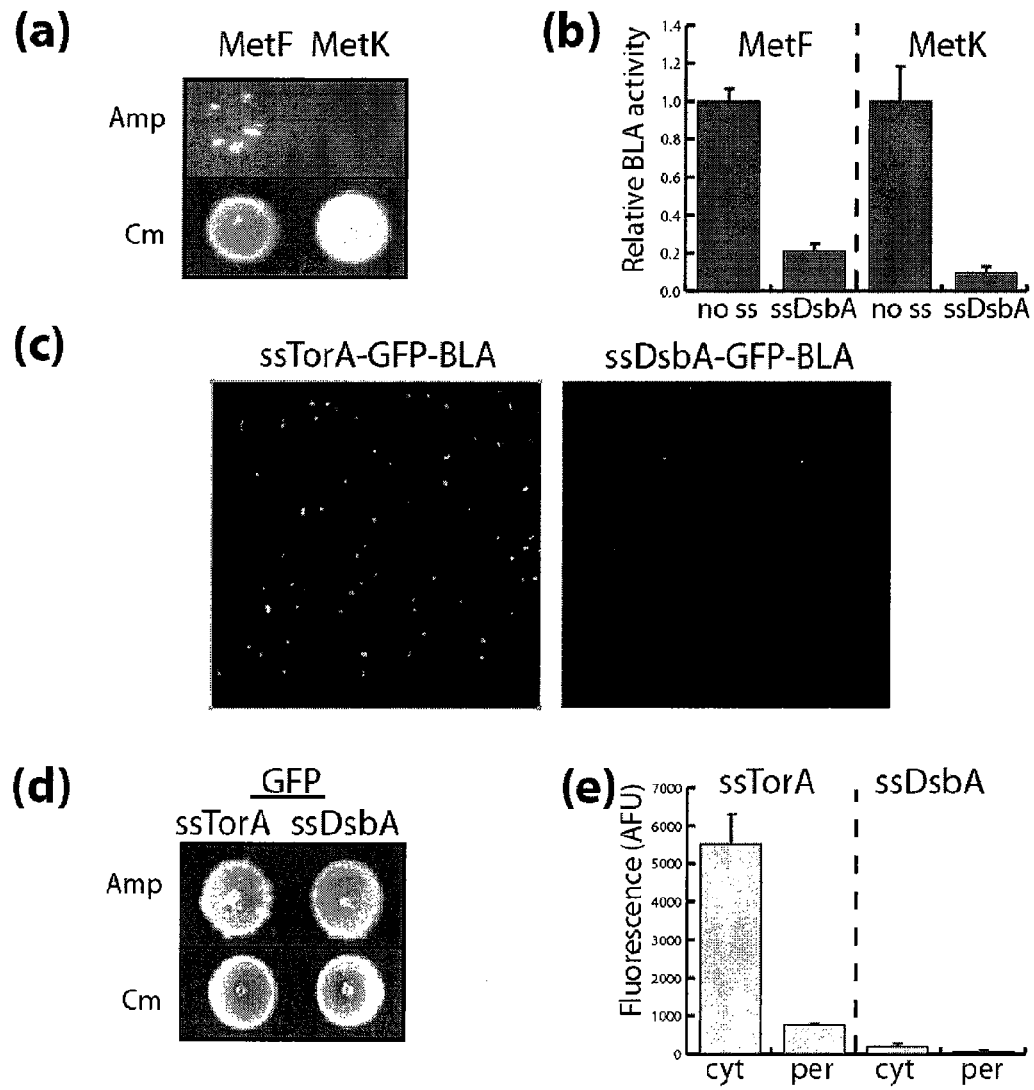
FIG. 3. Folding behavior of proteins requiring cytoplasmic chaperones and GFP. (a) MetF and MetK-containing fusions were spot plated as in FIG. 1c. (b) The nitrocefin hydrolysis activity of whole-cell lysates of ssDsbA-MetF/K-Bla and MetF/K-Bla with no signal sequence was measured as the initial velocity of absorbance change at 486 nm. Relative Bla activity was obtained by normalizing to the activity of the lysate without signal sequence. Bla activity was measured in triplicate and error bars represent standard error. (c) Fluorescence microscopy images at 100× of DH5α cells containing either pTMB-GFP or pDMB-GFP. (d) Spot plating of cells containing pTMB-GFP and pDMB-GFP as in FIG. 1c. (e) Fluorescence of subcellular fractions of ssTorA-GFP-Bla and ssDsbA-GFP-Bla. Fluorescence measurements were performed in triplicate and error bars represent standard error. AFU, arbitrary fluorescence units.

Along similar lines to the above experiments, we hypothesized that proteins whose folding is dependent on cytoplasmic chaperone activity would not be able to fold in the periplasm and thus would not confer significant Amp resistance in the context of our assay. To test this, we created fusions between Bla and two components of the *E. coli* methionine biosynthesis pathway, MetF and MetK, both of which have been shown to require the cytoplasmic chaperone GroEL for folding. Houry, W. A., Frishman, D., Eckerskorn, C., Lottspeich, F. & Hartl, F. U. Identification of in vivo substrates of the chaperonin GroEL. *Nature* 402, 147-154 (1999); Kerner, M. J. et al. Proteome-wide analysis of chaperonin-dependent protein folding in *Escherichia coli*. *Cell* 122, 209-220 (2005). We predicted that these fusions would not fold in the periplasm since GroEL and sufficient levels of ATP are absent from this compartment. Missiakas, D. & Raina, S. Protein folding in the bacterial periplasm. *J Bacteriol* 179, 2465-2471 (1997). Indeed, spot-plating of MetF and MetK fusions on 100 □g/ml Amp confirmed our hypothesis, as very little resistance was conferred by either of these fusions (FIG. 3a). To ensure that the low Amp resistance was due to the lack of GroEL, we expressed the MetF and MetK fusions in the cytoplasm by cloning each without the DsbA signal peptide in pDMB. A comparison of the Bla activity from cell lysates revealed that fusions expressed in the cytoplasm exhibited high Bla activity as measured by nitrocefin hydrolysis whereas lysates of those directed to the periplasm by ssDsbA were relatively inactive (FIG. 3b). Thus, C-terminal fusions of Bla to MetF and MetK are active when expressed in an environment containing GroEL (the cytoplasm), but inactive when expressed in the absence of GroEL (the periplasm). Western blotting of subcellular fractions generated from cells expressing ssDsbA-MetF-Bla confirmed that this protein was present in the periplasm, albeit at low levels (data not shown), suggesting that the reason for the low resistance to Amp was due to failure of the fusion to attain a stable, folded conformation in the periplasm rather than a defect in protein export.

EXAMPLE 4

Unraveling the Folding and Solubility of GFP in the Periplasm

Despite the widespread use of GFP as a reporter of protein activity in the cytoplasm of *E. coli*, including as a folding reporter, proper folding of GFP in the periplasm of *E. coli* has been challenging. Interestingly, when translocated via the Sec pathway, GFP is detectable in the soluble fraction of cell lysate, yet fails to attain its fluorescent conformation for unknown reasons. Feilmeier, B. J., Iseminger, G., Schroeder, D., Webber, H. & Phillips, G. J. Green fluorescent protein functions as a reporter for protein localization in *Escherichia coli*. *J Bacteriol* 182, 4068-4076 (2000). If this were true, we would expect an ssDsbA-GFP-Bla fusion to be non-fluorescent but to confer growth to cells due to the periplasmic solubility of the GFP moiety. Indeed, cells expressing the ssDsbA-GFP-Bla fusion were non-fluorescent (FIG. 3c) but exhibited a strong Amp-resistant phenotype (FIG. 3d). For comparison, targeting of GFP-Bla to the Tat pathway resulted in highly fluorescent cells (FIG. 3c) that were similarly Amp-resistant (FIG. 3d), consistent with earlier findings. Fisher et al., supra. In agreement with the microscopy results, subcellular fractions from cells expressing ssTorA-GFP-Bla were highly fluorescent, whereas fractions obtained from cells expressing ssDsbA-GFP-Bla had dramatically lower fluorescence (FIG. 3e). Note that the periplasmic fraction of ssTorA-GFP-Bla is fluorescent because it has folded in the cytoplasm and is transported in a folded conformation. Fisher et al., supra.

EXAMPLE 5

Increased Solubility of Aggregating Proteins Increases Bla Activity

Figure 4:
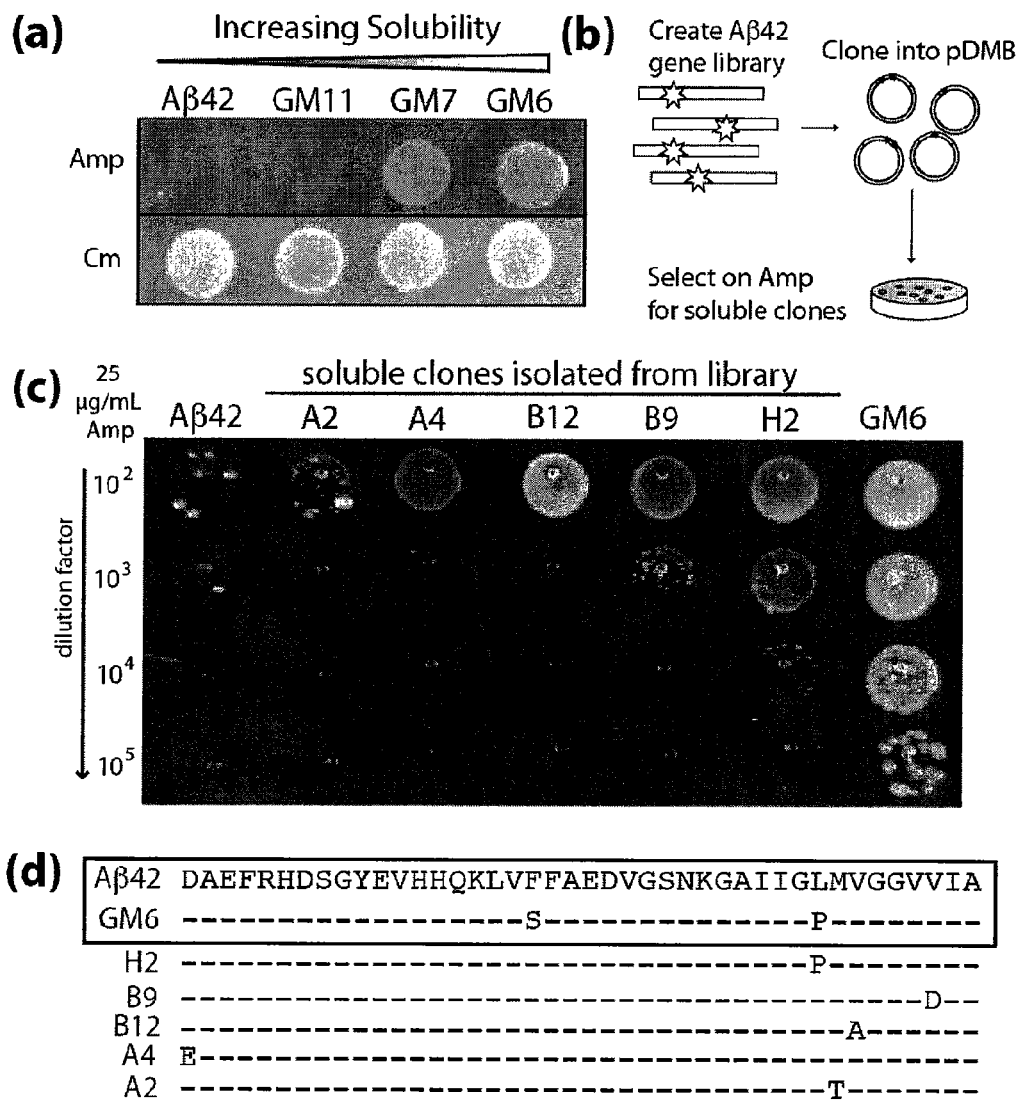
FIG. 4. Engineering solubility in the aggregating protein amyloid β 42. (a) Engineered soluble variants of Aβ42, GM7, GM11, and GM6, and wildtype Aβ42 were spot plated as in FIG. 1c. (b) Schematic for directed evolution of soluble proteins using the periplasmic folding reporter. (c) Spot plating of evolved variants of Aβ42 with greater solubility than wildtype at various dilution factors from overnight cultures, along with wildtype Aβ42 and soluble variant GM6. (d) Amino acid sequences of evolved higher-solubility peptides, along with Aβ42 and GM6 for comparison. Dashes (–) represent no change from wildtype.

We next sought to determine the feasibility of our system as a tool for isolating solubility-enhanced proteins using a directed evolution approach. For this purpose, we chose as a model POI the 42-residue amyloid p peptide (Aβ42). Aβ42 is highly prone to aggregation and is the primary constituent in dense amyloid fibrils known as plaques that accumulate in the brains of patients with Alzheimer's disease. Selkoe, D. J. Alzheimer's disease: genes, proteins, and therapy. *Physiol Rev* 81, 741-766 (2001). Just like in humans, Aβ42 aggregates extensively when expressed in the cytoplasm of *E. coli* and also in the periplasm as evidenced by the relative inability of ssDsbA-Aβ42-Bla to confer growth to cells (FIG. 4a). Interestingly, Hecht and coworkers, supra, isolated solubility-enhanced Aβ42 variants, namely GM11 (Aβ42H6Q/V12A/V24A/I32M/V36G), GM7 (V12A/I32T/L34P), and GM6 (F19S/L34P). Each of these conferred increased resistance to cells when expressed in the periplasm as a ssDsbA-Aβ42-Bla fusion (FIG. 4a). The most soluble variant, GM6, displayed an 8-fold higher MIC and MBC relative to Aβ42 wildtype (Table 1).

Encouraged by the observation that growth selection could be used to easily distinguish more soluble Aβ42 variants from the parental Aβ42 sequence, we proceeded to screen a combinatorial library of Aβ42 sequences with the goal of using simple Amp selection to isolate solubility-enhanced variants (FIG. 4b). An Aβ42 library was created by subjecting the gene encoding wildtype Aβ42 to error-prone PCR and then cloning the PCR library into pDMB, resulting in a library of ssDsbA-Aβ42 -Bla fusions with approximately 50,000 members. Plating of a portion of this library on 25 µg/ml Amp allowed us to recover 5 clones exhibiting an Amp-resistant phenotype above wildtype Aβ42 (FIG. 4c). Each of these variants showed at least 2-fold improvement in MIC and MBC over wildtype, with clone H2 having 4-fold higher MIC and MBC than wildtype (Table 1). Interestingly, clone H2 contains the L34P mutation (FIG. 4d), which is present in the previously engineered variants GM7 and GM6 and by itself (GM18) was sufficient to reduce Aβ42 aggregation. The other clones we isolated had point mutations within hydrophobic clusters near residue 34-A2 (M35T), B9 (V40D), and B12 (V37A) (FIG. 4d)—that have been implicated previously as key determinants in fibril formation. Dobeli, H. et al. A biotechnological method provides access to aggregation competent monomeric Alzheimer's 1-42 residue amyloid peptide. *Biotechnology* (N Y) 13, 988-993 (1995). It should be noted that this improvement in solubility came after only one round of directed evolution, and that only about 10,000 clones were screened.

EXAMPLE 6

Correlating β-lactamase activity with protein folding and solubility

To validate the present assay, a variety of proteins were analyzed that are known to have different folding properties in the periplasm. Examples of proteins that are known to not fold well in the periplasm are MetF, MetK, Aβ42, and PhoA. MetF and MetK are substrates of the cytoplasmic chaperone GroEL. Their proper folding is dependent on GroEL. Thus it is reasonable that folding in the periplasm is minimal Aβ42 is the amyloid β peptide, known for its tendency to aggregate in the brains of Alzheimer's patients. PhoA requires the formation of disulfide bonds to fold properly, so when it is produced in strain containing a reducing periplasm, it does not fold. These four proteins were cloned into the multiple cloning site of the vector between ssDsbA and Bla and the vectors introduced into DH5α cells (Aβ42, MetF, or MetK) or DHA cells which is similar to DHB4 and engineered to contain a reducing periplasmic environment (PhoA). Five ul aliquots of an overnight inoculum of cells were spot plated on 50 ug/mL chloramphenicol or 100 ug/mL ampicillin media plates and grown at 37 C for 16 hours. The cells demonstrated little growth on the ampicillin plates and near confluent growth on the chloramphenicol plates.

Engineered variants of the *E. coli* maltose binding protein and amyloid β peptide that have varying ability to fold in the periplasm were assayed next. Four variants each of maltose binding protein and amyloid β peptide were cloned into the multiple cloning site of the vector between ssDsbA and Bla and the vectors introduced into DH5α cells. Five ul aliquots of an overnight inoculum of cells were spot plated on 50 ug/mL chloramphenicol or 100 ug/mL ampicillin media plates and grown at 37 C for 16 hours. The variants with poor folding and solubility demonstrated little growth on the ampicillin plates, while the variants with better solubility demonstrated increasing amounts of growth on the ampicillin plates. The observed growth on the ampicillin correlated to the solubility of the variants of both maltose binding protein and amyloid β peptide and demonstrated that variants with intermediate solubility or folding ability in the periplasm exhibited intermediate amounts of growth on the ampicillin plates. The cells line grew to confluency on the control chloramphenicol plates.

Examples of *E. coli* proteins that fold and are soluble in the periplasm are MalE, PhoA, GST and TrxA. These four proteins were cloned into the multiple cloning site of the vector between ssDsbA and Bla and the vectors introduced into DH5α cells (Aβ42, MetF, or MetK) or DHB4 cells, a DH5α strain that is phoA- (PhoA). Five ul aliquots of an overnight inoculum of cells were spot plated on 50 ug/mL chloramphenicol or 100 ug/mL ampicillin media plates and grown at 37 C for 16 hours. The cells containing all four of these vectors exhibited confluent growth after 16 hours on ampicillin plates and essentially equivalent growth on control chloramphenicol plates. Growth on the selective ampicillin plates correlated to a high ability of the assayed proteins to fold and be soluble in the periplasm.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of screening for protein variants that fold correctly in the periplasm comprising:
   providing a library of nucleic acid sequences encoding a signal sequence, variant target protein sequence, and reporter sequence in operable combination, wherein said signal sequence is a signal sequence recognized by the signal recognition particle (SRP)-dependent pathway;
   expressing said library of nucleic acid sequences in cells; and
   correlating reporter activity to the correct folding of variant target proteins in the periplasm of the cells.

2. The method of claim 1, wherein said correlating further comprises growing said cells on selective media, wherein said reporter gene sequence allows growth of cells in which said fusion protein is correctly folded in the periplasm of said cells on said selective media.

3. The method of claim 1, wherein said reporter gene sequence is the beta-lactamase gene sequence.

4. The method of claim 2, further comprising the step of selecting clones of said cells that grow on said selective media.

5. The method of claim 1, wherein said target protein is selected from the group consisting of an amyloid-β peptide and a single-chain Fv antibody fragment.

6. A method for high-throughput screening of target proteins that fold correctly in the periplasm comprising:
providing a library of nucleic acid sequences encoding a signal sequence, target protein sequence, and reporter sequence in operable combination, wherein said signal sequence is a signal sequence recognized by the signal recognition particle (SRP)-dependent pathway;
introducing said library of nucleic acid sequences into cells;
growing said cells on a selective media, wherein said reporter gene sequence allows growth on said selective media of cells in which said fusion protein is correctly folded in the periplasm of said cells; and
selecting clones of said cells in which said fusion protein is correctly folded in the periplasm.

7. The method of claim 6, further comprising the steps of further culturing said clones of said cells in which said fusion protein is correctly folded in the periplasm and isolating said fusion protein from said cells.

8. The method of claim 6, further comprising the steps of subcloning said target protein sequence, expressing the target protein sequence in a desired cell line, and purifying said target protein sequence from said desired cell line.

9. A library of cells comprising a plurality of nucleic acid sequences comprising a signal sequence, variant target protein sequence, and reporter sequence in operable combination.

10. A library of cells comprising a plurality of nucleic acid sequences comprising a signal sequence, target protein sequence, and reporter sequence in operable combination, wherein said plurality of nucleic acid sequences comprise different target protein sequences.

11. A library of nucleic acid sequences comprising a signal sequence, variant target protein sequence, and reporter sequence in operable combination.

12. A library of nucleic acid sequences comprising a signal sequence, target protein sequence, and reporter sequence in operable combination, wherein said plurality of nucleic acid sequences comprise different target protein sequences.

* * * * *

UNITED STATES PATENT AND TRADEMARK OFFICE
CERTIFICATE OF CORRECTION

PATENT NO. : 8,722,584 B2 Page 1 of 1
APPLICATION NO. : 12/522634
DATED : May 13, 2014
INVENTOR(S) : Delisa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 525 days.

Signed and Sealed this

Twenty-ninth Day of September, 2015

Michelle K. Lee
*Director of the United States Patent and Trademark Office*